(12) United States Patent
Kluttz et al.

(10) Patent No.: US 6,410,275 B1
(45) Date of Patent: *Jun. 25, 2002

(54) DISPOSABLE TEST DEVICES FOR PERFORMING NUCLEIC ACID AMPLIFICATION REACTIONS

(75) Inventors: Bryan Kluttz, Norwell; Lawrence Burg, Framingham, both of MA (US); Garry Tegeler, Hazelwood, MO (US); Louis Graziano, Rockland, MA (US); Christopher Cotter, Charlestown, MA (US); Michel Guy, Scituate, MA (US); James Greer, Rockland, MA (US); Geoff McKinley; Luigi Catanzariti, both of Duxbury, MA (US); Robert Glassfold, West Warwick, RI (US); James Clement Bishop, Columbia, MO (US); Bruno Colin, Marcy l'Etoile (FR); Cécile Paris, Lyons (FR); Thomas Wang, Lexington; Michael Morin, Dedham, both of MA (US)

(73) Assignee: bioMerieux, Inc., Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/420,139

(22) Filed: Oct. 18, 1999

Related U.S. Application Data

(63) Continuation-in-part of application No. 09/053,823, filed on Apr. 2, 1998, now Pat. No. 5,989,499, which is a continuation-in-part of application No. 08/850,207, filed on May 2, 1997, now Pat. No. 5,786,182.

(51) Int. Cl.[7] ........................ C12P 19/34; C12M 3/00; G01N 21/00; C12N 15/00

(52) U.S. Cl. ................ 435/91.1; 435/91.2; 435/285.1; 435/287.2; 435/287.3; 435/287.6; 435/288.5; 422/64; 422/101; 422/102; 935/78; 935/87; 935/88

(58) Field of Search ........................ 435/91.1, 91.2, 435/91.5, 285.1, 287.2, 287.3, 287.6, 287.9, 288.2, 288.5, 286.1; 422/64, 101, 102; 935/78, 87, 88

(56) References Cited

U.S. PATENT DOCUMENTS

| 3,579,303 A | 5/1971 | Pickering |
| 3,833,406 A | 9/1974 | White ........................ 117/97 |
| 3,994,594 A | 11/1976 | Sandrock et al. |
| 4,038,151 A | 7/1977 | Fadler et al. ................ 195/127 |

(List continued on next page.)

FOREIGN PATENT DOCUMENTS

| EP | 0320752 | 6/1989 | |
| EP | 0469309 | 2/1992 | |
| EP | 0573098 | 12/1993 | ............. B01L/3/00 |
| EP | 0636413 | 2/1995 | |

(List continued on next page.)

OTHER PUBLICATIONS

Search Report in European Patent Application No. 01203068.0 of bioMerieux, Inc. dated Sep. 11, 2001.
*Mini VIDAS Operators Manual, bioMérieux Vitek, Inc. (1995).

(List continued on next page.)

Primary Examiner—David A. Redding
(74) Attorney, Agent, or Firm—McDonnell Boehnen Hulbert & Berghoff

(57) ABSTRACT

A unit dose test device for a nucleic acid amplification reaction has the form of a elongate disposable test strip. The test strip includes a dual-chamber reaction vessel pre-loaded with nucleic acid amplification reaction reagents, and a plurality of wells for processing a reaction occurring in the reaction vessel.

37 Claims, 17 Drawing Sheets

U.S. PATENT DOCUMENTS

| | | | |
|---|---|---|---|
| 4,043,678 A | 8/1977 | Farrell | 356/246 |
| 4,106,675 A | 8/1978 | Taylor | 222/556 |
| 4,116,775 A | 9/1978 | Charles et al. | 195/103.5 |
| 4,119,407 A | 10/1978 | Goldstein et al. | 422/58 |
| 4,195,060 A | 3/1980 | Terk | 422/61 |
| 4,207,394 A | 6/1980 | Aldridge et al. | 435/34 |
| 4,267,833 A | 5/1981 | Barger et al. | 128/213 |
| 4,330,627 A | 5/1982 | Thomas et al. | 435/301 |
| 4,332,769 A | 6/1982 | Rampy et al. | 422/745 |
| 4,605,536 A | 8/1986 | Kuhnert | 422/99 |
| 4,943,522 A | 7/1990 | Eisinger et al. | 435/7 |
| 4,956,148 A | 9/1990 | Grandone | 422/64 |
| 5,229,297 A | 7/1993 | Schnipelsky et al. | 436/94 |
| 5,270,183 A | 12/1993 | Corbett et al. | |
| 5,324,481 A | 6/1994 | Dunn et al. | 422/64 |
| 5,437,990 A | 8/1995 | Burg et al. | 435/91.2 |
| 5,498,392 A | 3/1996 | Wilding et al. | 425/68.1 |
| 5,510,084 A | 4/1996 | Cros et al. | 422/104 |
| 5,554,516 A | 9/1996 | Kacian et al. | 435/91.21 |
| 5,567,617 A | 10/1996 | Caprio et al. | 435/287.2 |
| 5,587,128 A | 12/1996 | Wilding et al. | 422/50 |
| 5,602,037 A | 2/1997 | Ostgaard et al. | 436/69 |
| 5,605,665 A | 2/1997 | Clark et al. | 422/102 |
| 5,645,801 A | 7/1997 | Bouma et al. | 422/68.1 |
| 5,725,831 A | 3/1998 | Reichler et al. | 422/56 |
| 5,783,148 A | 7/1998 | Cottingham et al. | 422/56 |
| 5,786,182 A | 7/1998 | Catanzariti et al. | 435/91.1 |
| 5,888,826 A | 3/1999 | Ostgaard et al. | 436/69 |
| 5,989,499 A | 11/1999 | Catanzariti et al. | 422/63 |
| 6,238,910 B1 | 5/2001 | Custance et al. | 435/287.2 |

FOREIGN PATENT DOCUMENTS

| | | | |
|---|---|---|---|
| EP | 0674009 | 9/1995 | C12Q/1/68 |
| EP | 0693560 | 1/1996 | C12Q/1/68 |
| EP | 0726310 | 8/1996 | C12N/9/12 |
| EP | 0875291 | 11/1998 | B01L/3/00 |
| FR | 2612297 | 3/1987 | |
| JP | 7265100 | 10/1995 | |
| JP | 8275800 | 10/1996 | |
| JP | 9262084 | 10/1997 | |
| WO | WO9511083 | 4/1995 | |
| WO | WO9534684 | 12/1995 | |
| WO | WO9702357 | 1/1997 | |
| WO | WO9703348 | 1/1997 | G01N/21/00 |

OTHER PUBLICATIONS

*Brochure materials, VIDAS automated immunoanalyzer system, bioMérieux Vitek, Inc. (1994).

Routine Identification of Mycobacterium Tuberculosis Complex Isolated by Automated Hybridization, Claude Mabilat, bioMérieux SA, 692810 Marcy L'Etolle, and Institute Pasteur, 693658 Lyon Cedex 07, France, Journal of Clinical Microbiology, pp. 2702–2705, Nov. 1994.

*Mini VIDAS automated immunoanalyzer system of bioMerieux Vitek, Inc. (see Mini VIDAS Operators Manual).

*VIDAS test strip for use in VIDAS system, available from bioMerieux, Vitek, Ic. (see pp. 3–17 of Mini Vidas Operators Manual).

European Search Report, Application No. EP 98 30 3296, Dec. 22, 1999.

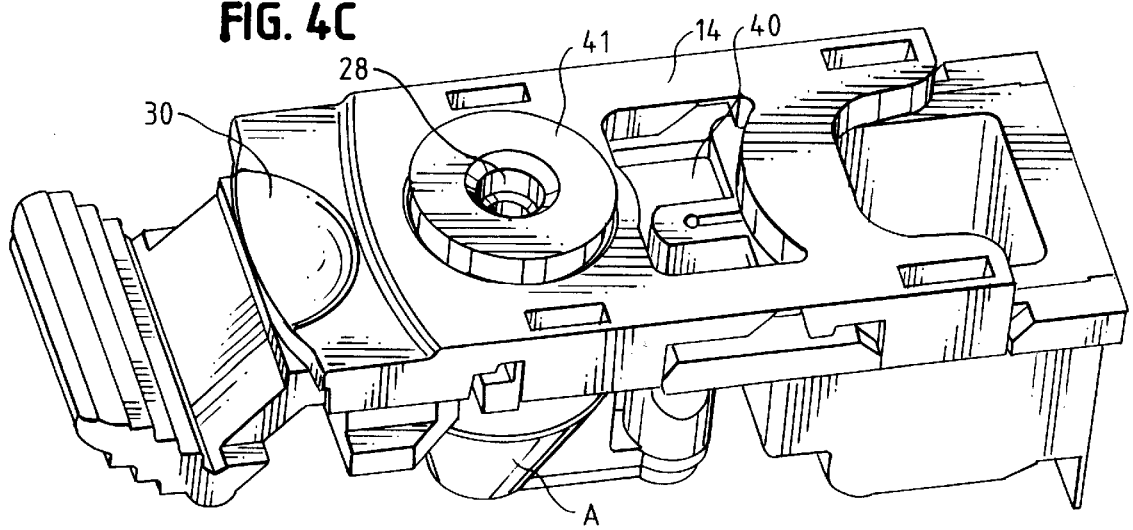
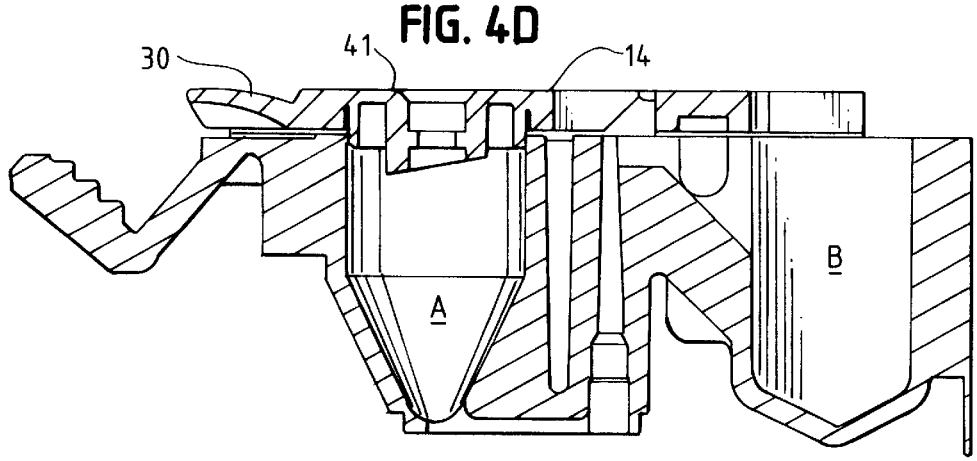
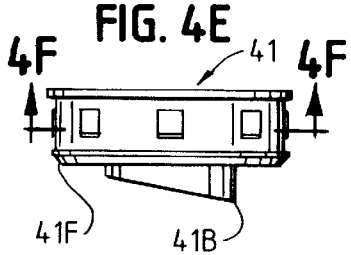
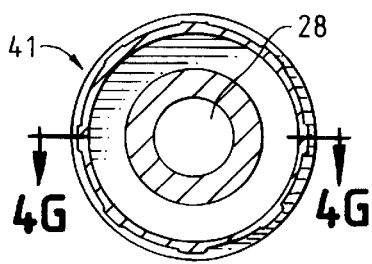
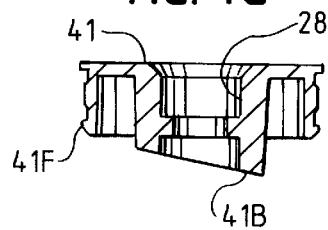

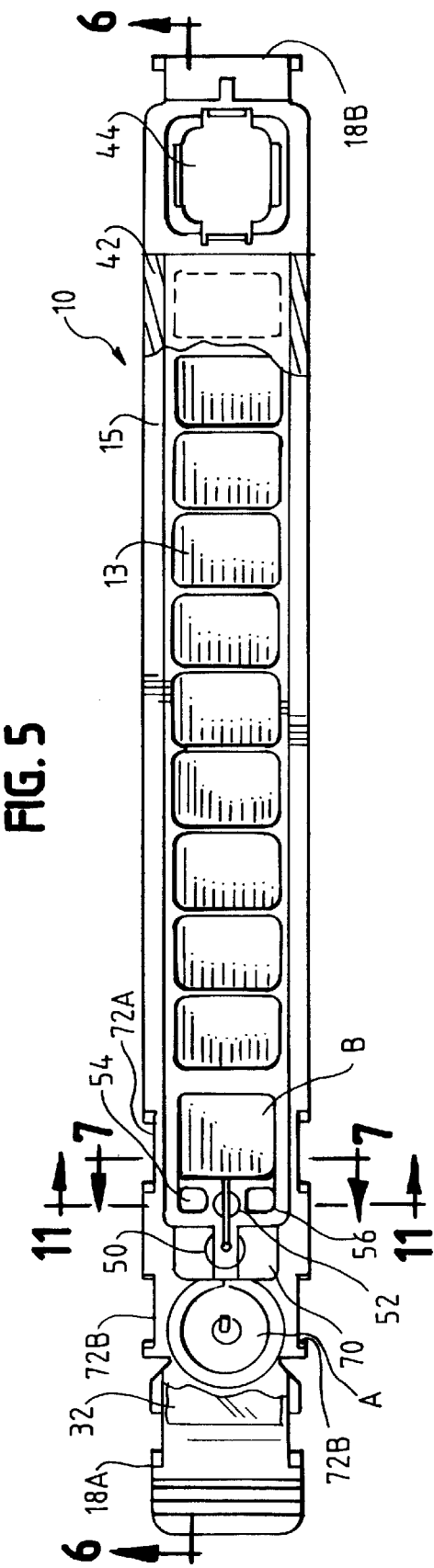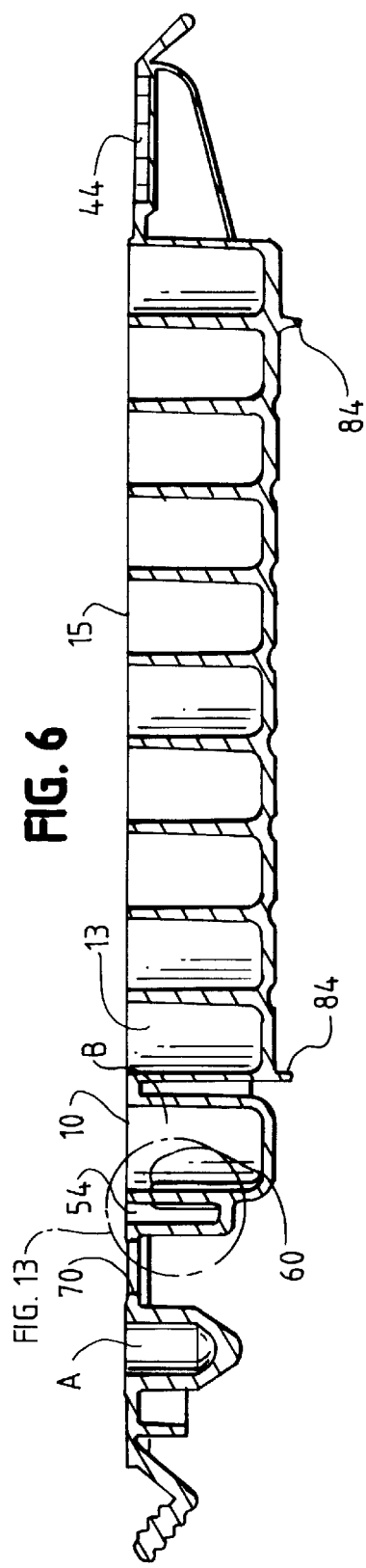

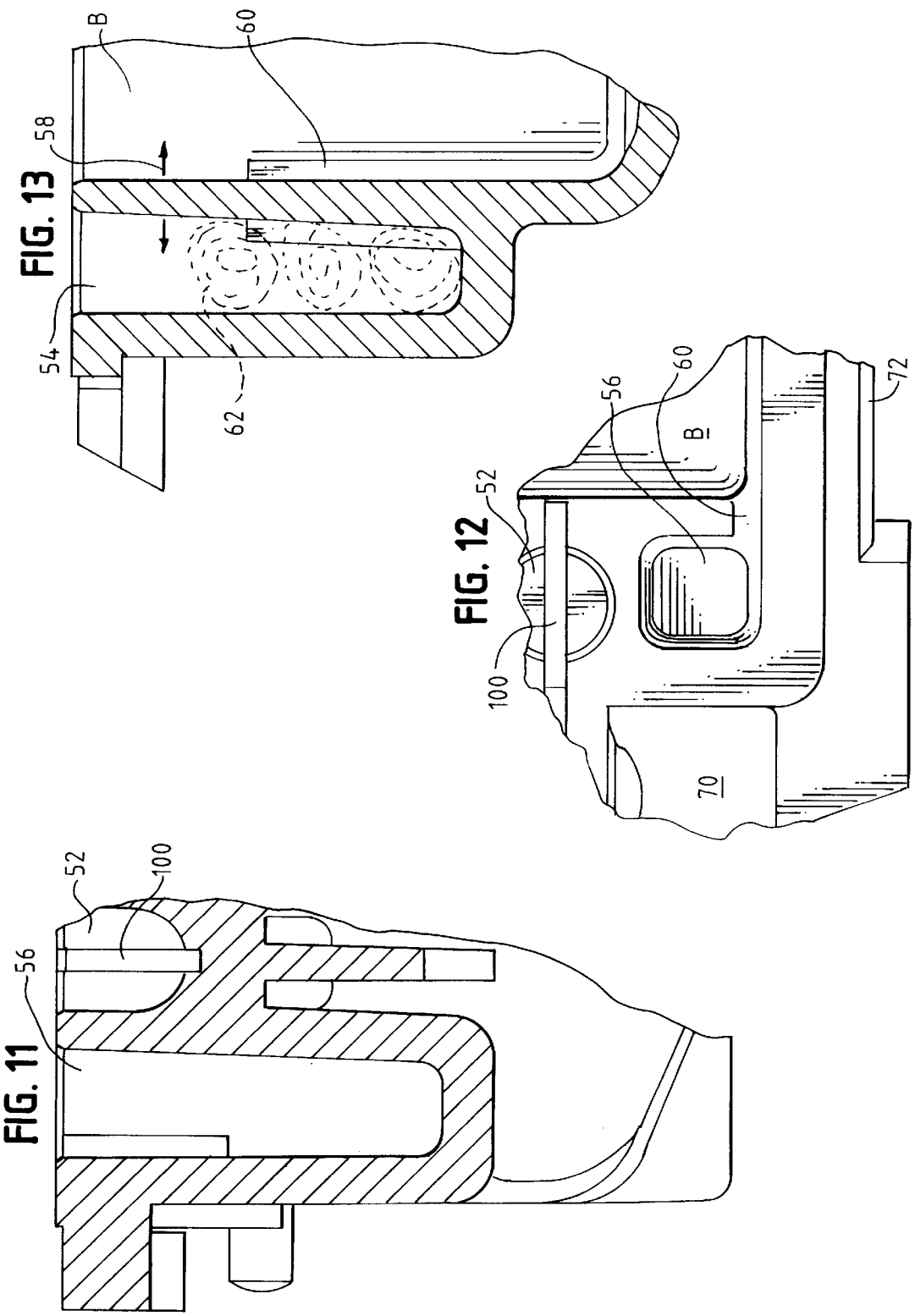

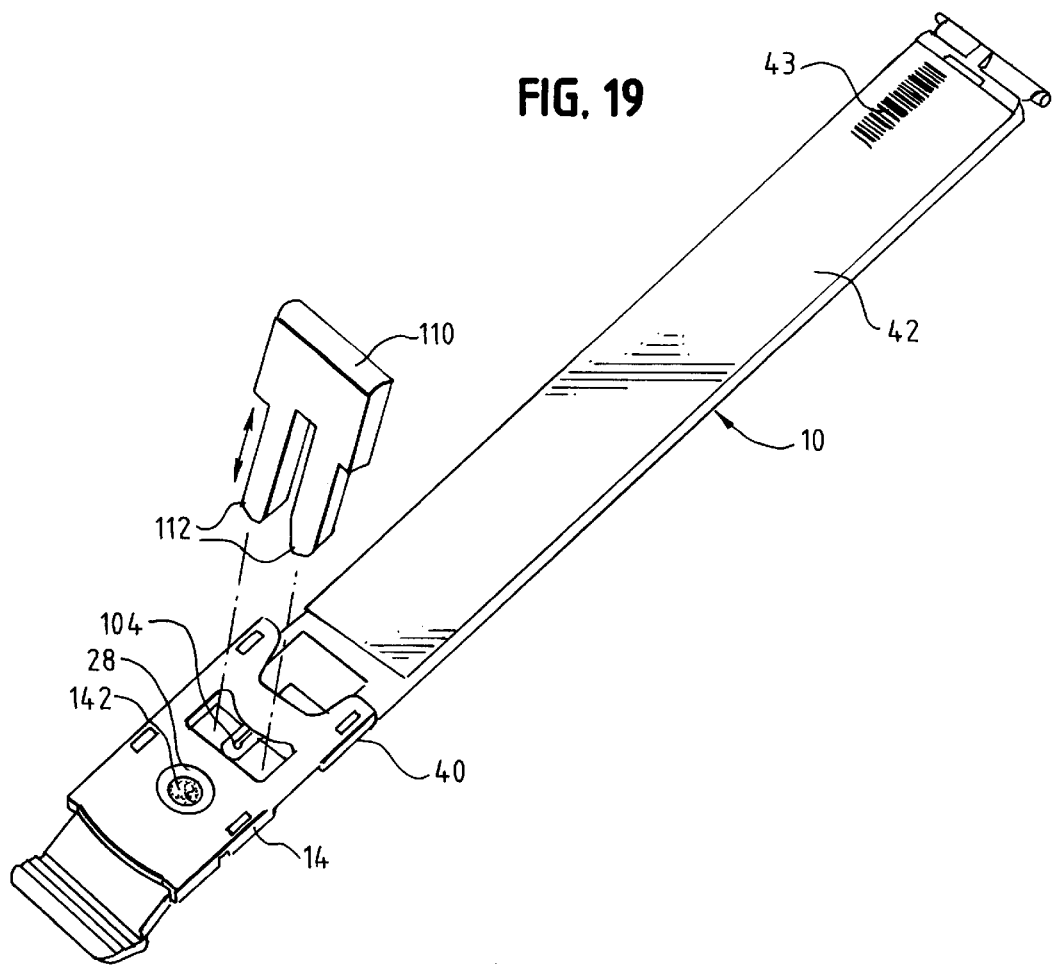
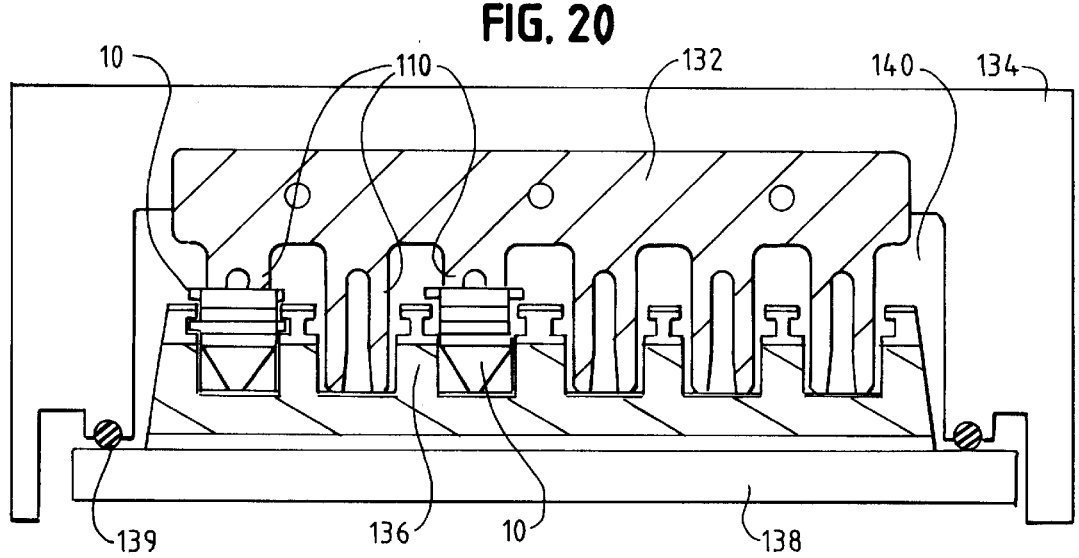

DISPOSABLE TEST DEVICES FOR PERFORMING NUCLEIC ACID AMPLIFICATION REACTIONS

CROSS-REFERENCE TO RELATED APPLICATIONS

This is a continuation-in-part of application Ser. No. 09/053,823 filed Apr. 2, 1998, now U.S. Pat. No. 5,989,499 which is a continuation-in-part of application Ser. No. 08/850,207 filed May 2, 1997, now U.S. Pat. No. 5,786,182. The entire contents of both of said related applications are fully incorporated by reference herein.

BACKGROUND OF THE INVENTION

A. Field of the Invention

This invention relates to the field of methods and devices for performing nucleic acid amplification reactions.

B. Description of Related Art

Nucleic acid based amplification reactions are now widely used in research and clinical laboratories for the detection of genetic and infectious diseases. The currently known amplification schemes can be broadly grouped into two classes, based on whether, after an initial denaturing step (typically performed at a temperature of $\geq 65$ degrees C.) for DNA amplifications or for RNA amplifications involving a high amount of initial secondary structure, the reactions are driven via a continuous cycling of the temperature between the denaturation temperature and a primer annealing and amplicon synthesis (or polymerase activity) temperature ("cycling reactions"), or whether the temperature is kept constant throughout the enzymatic amplification process ("isothermal reactions"). Typical cycling reactions are the Polymerase and Ligase Chain Reaction (PCR and LCR, respectively). Representative isothermal reaction schemes are NASBA (Nucleic Acid Sequence Based Amplification), Transcription Mediated Amplification (TMA), and Strand Displacement Amplification (SDA). In the isothermal reactions, after the initial denaturation step (if required), the reaction occurs at a constant temperature, typically a lower temperature at which the enzymatic amplification reaction is optimized.

Prior to the discovery of thermostable enzymes, methodologies that used temperature cycling were seriously hampered by the need for dispensing fresh polymerase into an amplification tube (such as a test tube) after each denaturation cycle, since the elevated temperature required for denaturation inactivated the polymerase during each cycle. A considerable simplification of the PCR assay procedure was achieved with the discovery of the thermostable Taq polymerase (from Thermophilus aquaticus). This improvement eliminated the need to open amplification tubes after each amplification cycle to add fresh enzyme. This led to the reduction of both the contamination risk and the enzyme-related costs. The introduction of thermostable enzymes has also allowed the relatively simple automation of the PCR technique. Furthermore, this new enzyme allowed for the implementation of simple disposable devices (such as a single tube) for use with temperature cycling equipment.

TMA requires the combined activities of at least two (2) enzymes for which no optimal thermostable variants have been described. For optimal primer annealing in the TMA reaction, an initial denaturation step (at a temperature of $\geq 65$ degrees C.) is performed to remove secondary structure of the target. The reaction mix is then cooled down to a temperature of 42 degrees C. to allow primer annealing. This temperature is also the optimal reaction temperature for the combined activities of T7 RNA polymerase and Reverse Transcriptase (RT), which includes an endogenous RNase H activity or is alternatively provided by another reagent. The temperature is kept at 42 degrees C. throughout the following isothermal amplification reaction. The denaturation step, which precedes the amplification cycle, however forces the user to add the enzyme to the test tube after the cool down period in order to avoid inactivation of the enzymes. Therefore, the denaturation step needs to be performed separately from the amplification step.

In accordance with present practice, after adding the test or control sample or both to the amplification reagent mix (typically containing the nucleotides and the primers), the test tube is subject to temperatures $\geq 65$ degrees C. and then cooled down to the amplification temperature of 42 degrees C. The enzyme is then added manually to start the amplification reaction. This step typically requires the opening of the amplification tube. The opening of the amplification tube to add the enzyme or the subsequent addition of an enzyme to an open tube is not only inconvenient, it also increases the contamination risk.

An alternative approach to amplification of a DNA sample is described in Corbett et al., U.S. Pat. No. 5,270,183. In this technique, a reaction mixture is injected into a stream of carrier fluid. The carrier fluid then passes through a plurality of temperature zones in which the polymerase chain reactions take place. The temperature of the different zones and the time elapsed for the carrier fluid to traverse the temperature zones is controlled such that three events occur: denaturation of the DNA strands, annealing of oligonucleotide primers to complementary sequences in the DNA, and synthesis of the new DNA strands. A tube and associated temperature zones and pump means are provided to carry out the '183 patent process.

The present invention avoids the inconvenience and contamination risk described above by providing a novel test device in the form of a strip that includes a dual chamber or "binary" reaction vessel, and a manner of using the device. The invention achieves the integration of the denaturation step with the amplification step without the need for a manual enzyme addition and without exposing the amplification chamber to the environment. The contamination risks from sample to sample contamination within the processing station are avoided since the amplification reaction chamber is sealed and not opened to introduce the patient sample to the enzyme. Contamination from environmental sources is avoided since the amplification reaction chamber remains sealed. The risk of contamination in nucleic acid amplification reactions is especially critical since large amounts of the amplification product are produced. The present invention provides a reaction chamber design that substantially eliminates these risks.

The preferred test strip embodiment allows the test device to be used in a currently installed instrument base after the performance of the amplification reaction, namely the VIDAS® instrument manufactured and distributed by the assignee of the present invention, bioMérieux, Inc. Thus, providing test devices in a size and configuration to be readily used in an existing instrument base allows the devices to be commercialized and used with a reduced capital expenditure and without having to develop a new instrument for processing the reaction and detecting the resulting amplicons. It will be apparent, however, from the following detailed description that the invention can be practiced in other configurations from the presently preferred embodiment described in detail herein.

SUMMARY OF THE INVENTION

In a preferred form of the invention, a dual chamber reaction vessel is provided which comprises a single or unit dose of reagents for a reaction requiring differential heat and containment features, such as a nucleic acid amplification reaction (for example, TMA reaction) packaged ready for use. The dual chamber reaction vessel is designed as a single use disposable unit. The reaction vessel is preferably integrally molded into a test device, such as a strip, having a set of wash and reagent wells for use in a amplification product detection station. Alternatively, the reaction vessel can be made as a stand alone unit with flange or other suitable structures for being able to be installed in a designated space provided in such a test device.

In the dual chamber reaction vessel, two separate reaction chambers are provided in a preferred form of the invention. The two main reagents for the reaction are stored in a spatially separated fashion. One chamber has the heat stable sample/amplification reagent (containing primers, nucleotides, and other necessary salts and buffer components in a reaction solution), and the other chamber contains the heat labile enzymatic reagents, e.g., T7 and RT. Alternatively, the heat labile enzymatic reagents may be stored in an intermediate chamber or well in fluid communication with the second chamber, such that a reaction solution from the first chamber flows through the intermediate chamber en route to the second chamber.

A fluid channel extending from the first chamber to the second chamber links the two chambers to each other. A means is provided for controlling or allowing the flow of fluid through the fluid channel from the first chamber to the second chamber. Various fluid flow control means are contemplated, such as providing a valve in the fluid channel, as described in the application Ser. No. 09/053,823 filed Apr. 2, 1998, now U.S. Pat. Nos. 5,989,499 and 5,786,182. Several different valve embodiments are described therein.

In use, the fluid sample is introduced into the first chamber and the first chamber is heated to a denaturation temperature (e.g., 95 degrees C.). After the amplification reagents in the first chamber have reacted with the fluid sample and the denaturation process has been completed, the first chamber is cooled to 42 degrees C. for primer annealing. The two chambers of the reaction vessel are not in fluid communication with each other prior to completion of the denaturation and cooling step. After these steps are complete, the means for controlling the flow of fluid is operated to allow the reaction solution to pass through the fluid channel from the first chamber to the second chamber. For example, the valve in the fluid channel is opened and the fluid sample is directed into the second chamber either by pressure or vacuum techniques. The reaction solution is then brought into contact with the amplification enzyme(s) (e.g., T7 and/or RT) and the enzymatic amplification process proceeds in the second chamber at 42 degrees C.

In a preferred embodiment, after completion of the amplification reaction, an SPR® (a fluid transfer, pipette-like device that functions as solid phase receptacle) is introduced into the second chamber. The test strip contains a plurality of wells arranged in an array. Hybridization, washing and optical analysis then proceeds in the wells in accordance with well known techniques in order to detect the amplification products. Such processes may occur in the adjacent wells of a test strip embodiment of the dual chamber reaction vessel automatically in an automated instrument, such as the VIDAS® instrument of bioMérieux, Inc.

Thus, a preferred form the present invention comprises a test strip for performing a nucleic acid amplification reaction. The test strip includes an integral, elongate housing formed in a strip having a first end and a second end, with the housing having a portion thereof defining a plurality of wells arranged in a linear array disposed in the strip between the first and second ends. The wells will be typically used for hybridization, washing or other detection and decontamination steps after the nucleic acid amplification reaction has been completed.

The test strip housing includes a dual chamber reaction vessel for a nucleic acid amplification reaction to be carried out therein, positioned adjacent to the first end of the test strip. The dual chamber reaction vessel comprises (1) a first chamber in which a first portion of a nucleic acid amplification reaction is performed (e.g., denaturation and primer annealing), (2) a second chamber in which a second portion of a nucleic acid amplification reaction is performed, (e.g., amplification of nucleotides by an amplification enzyme), and (3) an openable connecting conduit linking the first chamber to the second chamber.

In manufacture of the test strip, a first reagent (e.g., primers and/or nucleotides) is inserted into the first chamber for the first portion of the nucleic acid amplification reaction, and a second reagent (e.g., an amplification enzyme) is either inserted into or placed in fluid communication with the second chamber. After the reagents are loaded into the two chambers of the dual chamber reaction vessel (and any required reagent(s) inserted into the remaining wells of the test strip), a membrane is affixed to the test strip housing. The membrane is applied to the housing to cover the first and second chambers and the wells. Separate reagent loading steps and covering may be provided. Such other reagents can be used in other reaction steps for analysis of the test sample.

In order to prolong the shelf life of the test strips and reagents contained therein, a desiccant may be placed into the test strip, preferreably in communication with either the first or second chambers of the dual chamber reaction vessel. Alternatively, the desiccant may be molded into the material forming the test strip housing.

In order to provide a means for decontaminating the test strip before removing it from the instrument, a decontamination solution or bleach wash is provided in one of the sealed wells.

BRIEF DESCRIPTION OF THE DRAWINGS

A presently preferred embodiment of the invention is described below in conjunction with the appended drawing figures, wherein like reference numerals refer to like elements in the various views, and in which:

FIGS. 4C and 4D are views of still another alternative embodiment of the cover member;

FIGS. 4E, 4F, and 4G are detailed views of the button of FIGS. 4C and 4D;

FIG. 5 is a top plan view of the test strip of FIGS. 1–3;

FIG. 6 is a cross-sectional view of the test strip of FIG. 5, shown along the lines 6—6 of FIG. 5;

FIG. 11 is a cross-sectional view of the test strip of FIG. 5 taken along the lines 11—11 of FIG. 5, shown partially broken away, illustrating the desiccant well and enzyme pellet wells;

FIG. 12 is a detailed plan view of the desiccant well and adjacent structures in the test strip of FIG. 5;

FIG. 13 is a detailed sectional view of the desiccant well and a portion of the second reaction chamber of the test strip of FIG. 5;

FIG. 19 is a perspective view of a test strip of the kind shown in FIG. 5 with a fork implement used to open up the connecting conduit, with the arrow indicating the relative motion of the fork with respect to the test strip and the dotted lines indicating the insertion of the prongs of the fork into the test strip to open the ball valve in the connecting conduit;

FIG. 20 is a schematic illustration of a vacuum station incorporating a thermo-electric cooling (TEC)/heat sink thermal control system for the test strip and having a housing that engages a support structure to form a vacuum enclosure around the test strips, with each test strip associated with a fork for opening the connecting conduit when the vacuum chamber housing moves down and engages the support structure;

DETAILED DESCRIPTION OF THE PREFERRED EMBODIMENT

A preferred form of the invention provides for a dual chamber or "binary" reaction vessel embodied in a test strip or other configuration. The term "binary" refers to the characteristic of the vessel of storing in a spatially separated fashion at least two different reagents, for example a heat stable sample/amplification reagent(s) containing, for example, primers and nucleotides in one chamber and heat labile enzyme(s) such as T7 and RT in the second chamber. The reagents within the two chambers are not in contact prior to completion of the denaturation and cooling steps. The first chamber is accessible via a cap closure overlying a pierceable membrane or other means so as to permit an analytical or clinical or control sample(s) in liquid form to be added into the first chamber. The second chamber is sealed and contains the enzymatic components of the amplification reaction. The reagents may be in several physical forms, such as liquid, pelletized, lyophilized, etc. in unit dose amounts. After the contents of the first chamber is brought into contact with the second chamber, the amplification reaction can then take place, such as in the second chamber.

In one possible form of the invention, the two chambers may be part of an integrated disposable unit. In another possible embodiment, the two chambers may be two distinct units, which have complementary engaging surfaces, or features that allow the two units to be combined into a single unit. In the first embodiment, where the two chambers are part of a unitary article, the unit must be made to prohibit the exchange of materials between the two chambers during shipping and prior to the denaturation (heating) step. In both embodiments, a mechanism is required by which the contents of the first chamber (a solution containing the patient or test sample and amplification reagent(s) mix after denaturation and primer annealing) is brought into contact with the enzyme(s) in the second chamber. The mechanism operates to introduce the contents of the first chamber into the second chamber, following the completion of the denaturation step in the first reaction chamber at a temperature of ≧65 degrees C., and the cooling of the patient sample/amplification mix to the appropriate temperature for the enzymatic amplification reaction, e.g., 42 degrees C. Several different mechanisms are described in detail in U.S. Pat. No. 5,786,182.

Figure 1:
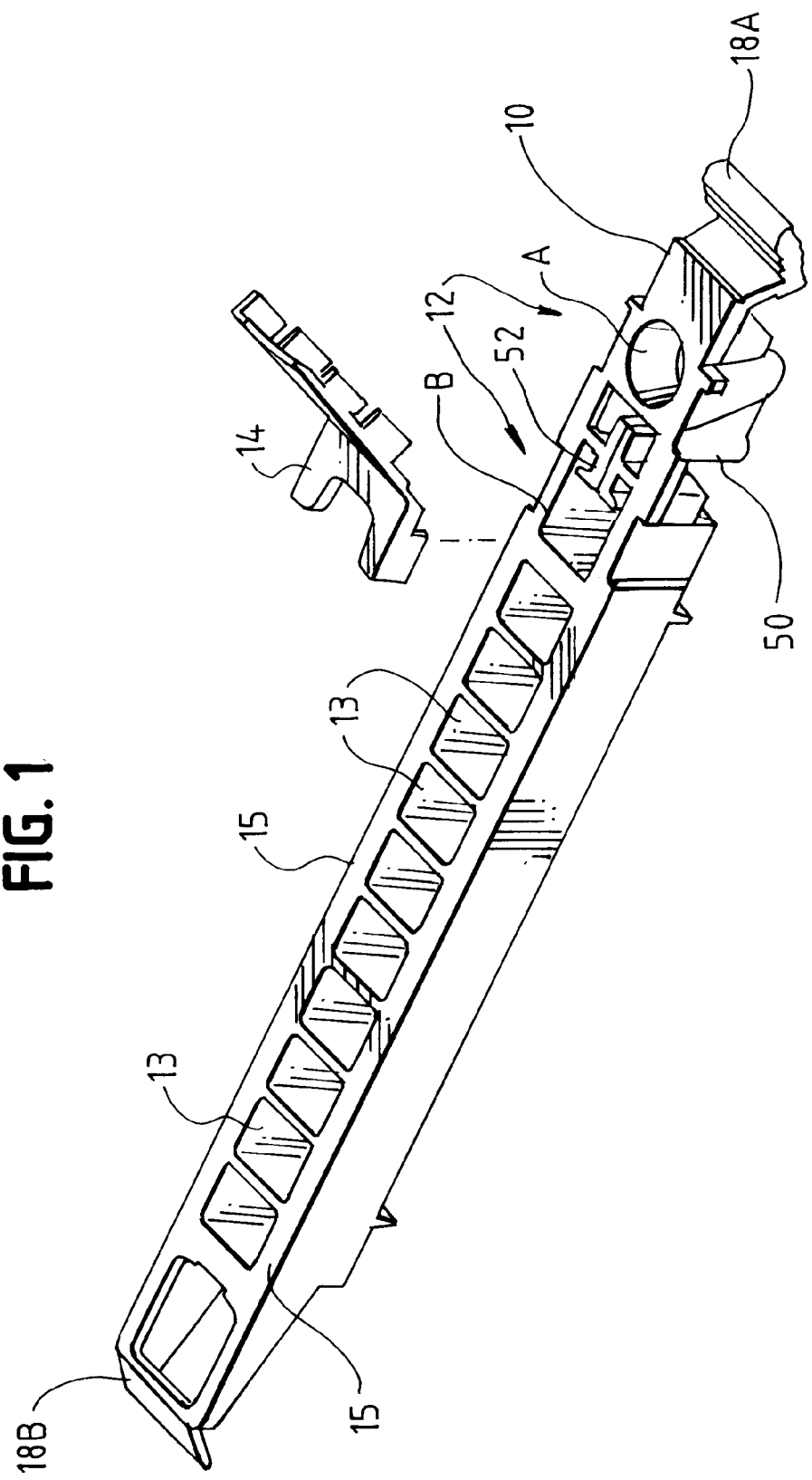
FIG. 1 is a perspective view of a test strip incorporating a dual chamber reaction vessel for a nucleic acid amplification reaction and associated cover member in accordance with a presently preferred embodiment of the invention, showing the cover member prior to attachment to the test strip in the vicinity of the dual chamber reaction vessel.

FIG. 1 is a perspective view of a test strip 10 incorporating a dual chamber reaction vessel 12 for a nucleic acid amplification reaction, a plurality of wells 13, and associated cover member 14 in accordance with a presently preferred embodiment of the invention. The test strip 10 of FIG. 1 is preferably made from a molded polymeric material, such as polypropylene.

A sealing membrane(s) is applied to the upper surface 15 of the test strip to cover the wells and dual chamber reaction vessel 12, after the wells and vessel 12 have been pre-loaded with the appropriate enzyme, reagents, wash or buffer solution, decontamination solution, etc. The membrane is not shown in FIG. 1 in order to better illustrate the structure of the test strip 10. The cover member 14 is shown prior to attachment to the test strip in the vicinity of the dual chamber reaction vessel 12.

The test strip of FIG. 1 can be used to perform a nucleic acid amplification reaction, e.g., a TMA reaction, in accordance with one possible embodiment of the invention. Chamber A of the dual chamber reaction vessel 12 contains the amplification reagents or mix, namely nucleotides, primers, $MgCl_2$ and other salt and buffer components. Chamber B is in fluid communication with a enzyme pellet well 52 that contains the amplification enzyme(s) that catalyzes the amplification reaction, e.g., T7 and/or RT. In an alternative embodiment, the amplification enzyme is loaded directly into chamber B.

After addition of the targets (or test sample) into chamber A, heat is applied to chamber A to denature the DNA nucleic acid targets and/or minimize RNA secondary structure. The temperature of chamber A is then cooled down to allow primer annealing. Subsequently, the solution of chamber A is brought into contact with an enzyme pellet in the pellet well 52 and the solution is introduced into chamber B. Chambers A and B, now in fluid communication with each other, are then maintained at the optimum temperature for the amplification reaction, e.g., 42 degrees C. By spatially separating chamber A from chamber B, and applying the heat for denaturation to chamber A only, the thermolabile enzymes are protected from inactivation during the denaturation step.

The controlled heating of dual chamber reaction vessel 12 in the test strip described above, and transfer of solution from Chamber A to Chamber B, is preferably performed in an amplification station or instrument designed to process the test strip 10. A preferred amplification station is described in U.S. Pat. No. 5,786,182, and in the patent application of Bryan Kluttz et al. filed concurrently, entitled "Nucleic Acid Amplification Reaction Station for Disposable Test Devices," Ser. No. 09/410,140, incorporated by reference herein.

After the reaction is completed, the test strip 10 is then processed in a machine such as the VIDAS® instrument commercially available from bioMérieux, Inc.

The test strip 10 of FIG. 1 is given a particular form factor (e.g., shape, length, width, height, end features 18A and 18B, etc.) so as to enable the test strip to be compatible with an existing or selected instrument base having a solid phase receptacle or other fluidic transfer means and other equipment for processing the results of the nucleic acid amplification reaction in the test strip per se. Thus, the preferred embodiment of the test strip 10 has a size and shape suitable for the VIDAS® instrument base of the inventors' assignee bioMerieux, Inc. It will appreciated that a different size, shape, configuration, and other physical characteristics of the test device incorporating the dual chamber reaction vessel can be arrived at to suit other analytic instruments, and other instruments that would conduct the nucleic acid amplification reaction in the dual chamber reaction vessel. Thus, the inventors do not consider the invention limited to the particular test strip form illustrated in the drawings.

Figure 2:
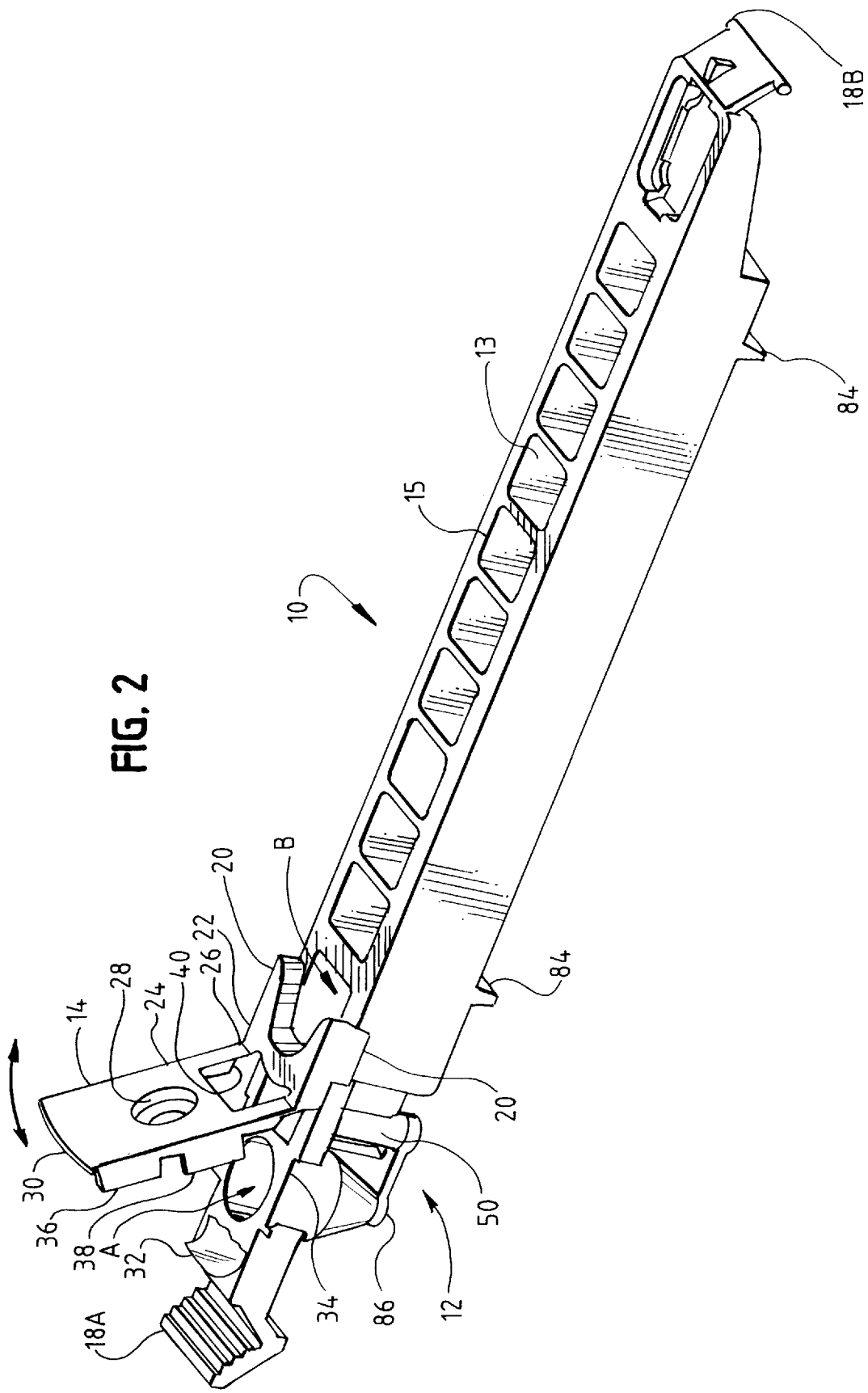
FIG. 2 is another perspective view of the test strip and cover member of FIG. 1, showing the cover member attached to the test strip and with a portion of the cover member in a raised or elevated position, allowing access to the first reaction chamber of the dual chamber reaction vessel therein.
Figure 3:
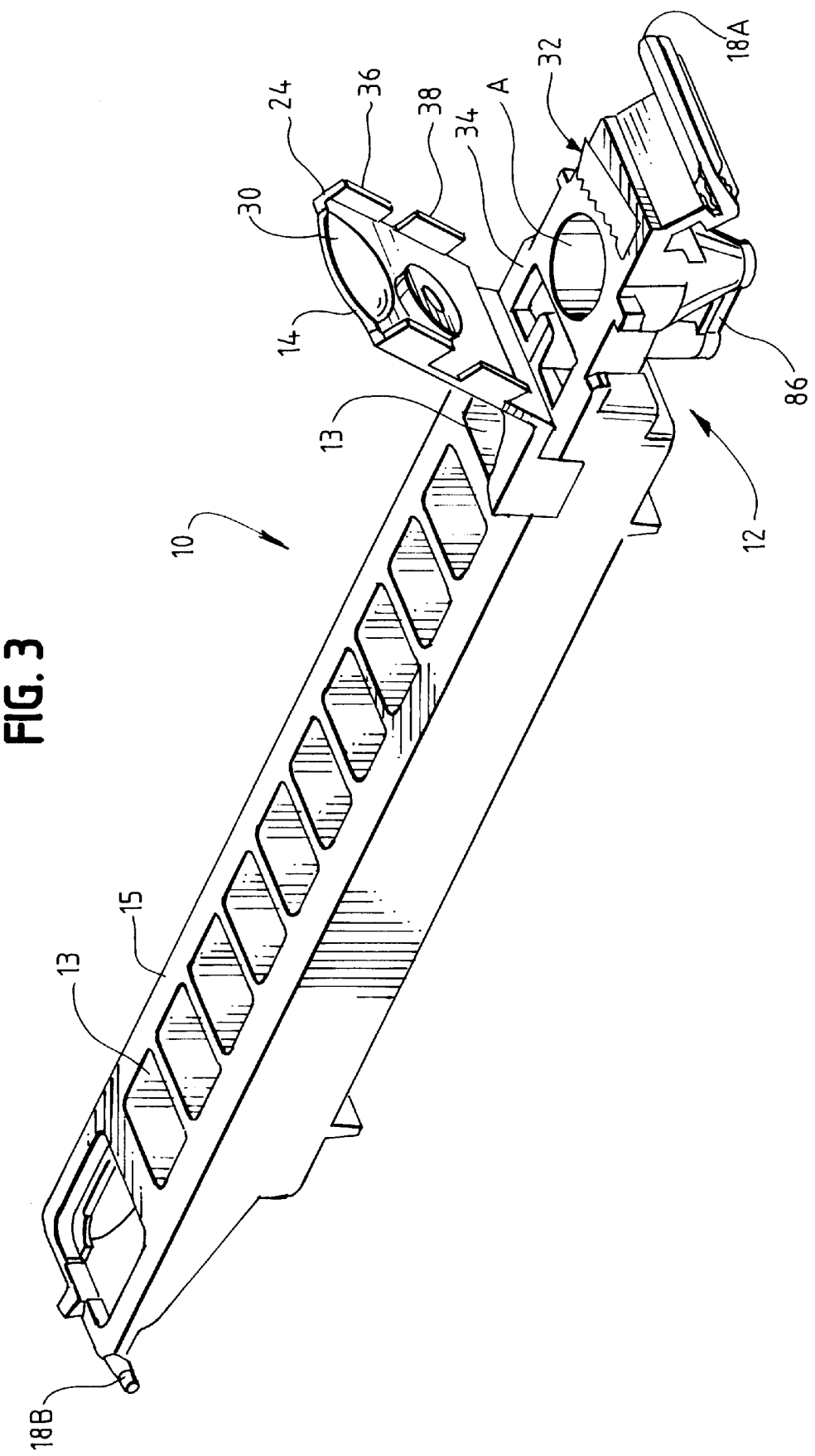
FIG. 3 is another perspective view of the test strip of FIG. 2.
Figure 4:
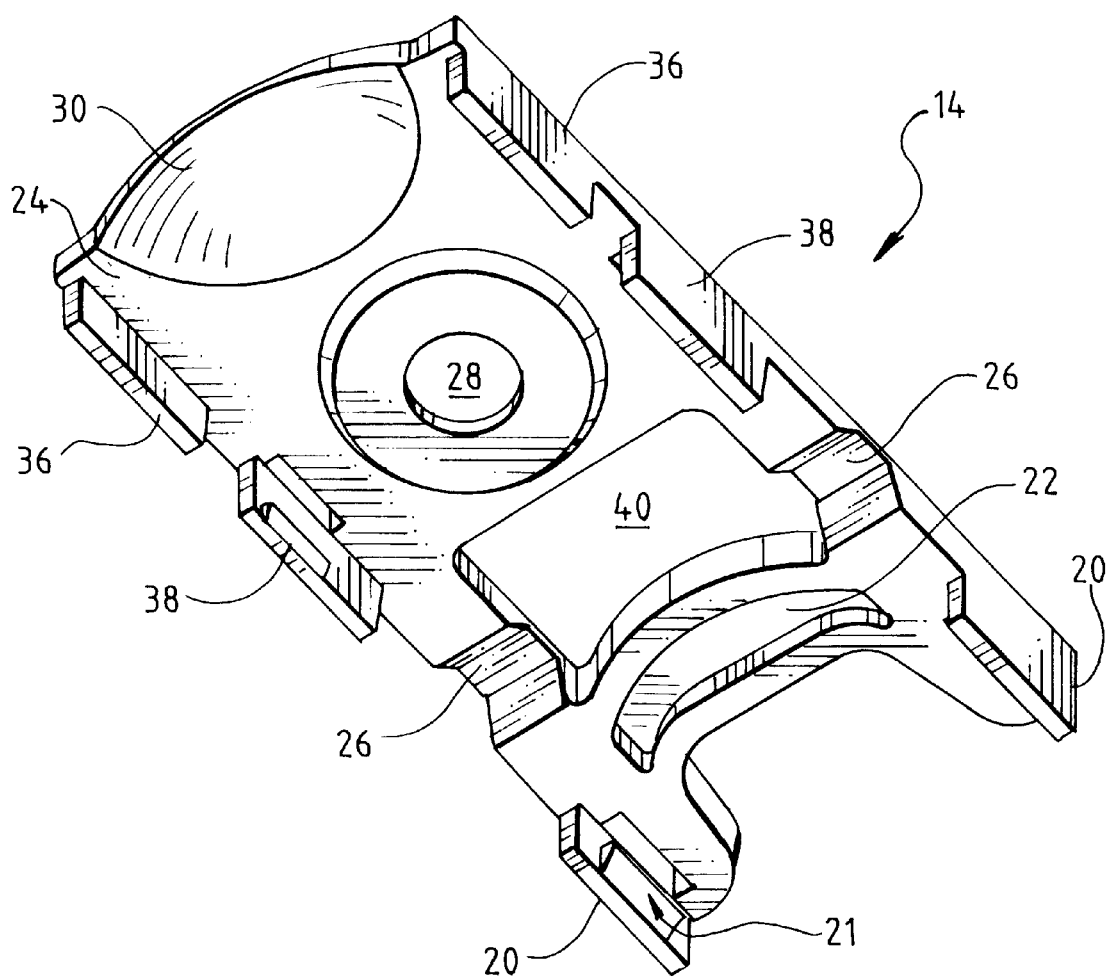
FIG. 4 is an isolated, perspective view of the cover member of FIGS. 1–3 shown from below.

FIGS. 2 and 3 are additional perspective views of the test strip 10 and cover member 14 of FIG. 1. FIG. 4 is an isolated perspective view of the cover member. Referring to FIGS. 2–4, the cover member 14 has a pair of resilient legs 20 with a wedge feature 21 that snap onto corresponding ledges formed in the upper edge of the test strip, as will be explained later in conjunction with FIGS. 7–10. The legs 20 allow the rear portion 22 of the cover 14 to be firmly and securely attached to the test strip 10, while allowing a second or forward portion 24 of the cover 14 to be raised and lowered relative to the rear portion 22. The cover 14, made of a molded polymeric material, includes an integral hinge portion 26 linking the portions 22 and 24 together. The cover also includes a central aperture 28 having a porous mesh filter placed therein to allow air to enter into or be removed from chamber A (after removal of the sealing membrane from the top of chamber A), while substantially blocking the escape of fluids or reagents from chamber A or the entry of foreign matter into chamber A.

The purpose of the cover 14 is to control access by the user to chamber A and to provide a protective barrier from the environment during the performance of the nucleic acid amplification reaction. During manufacture of the test strip, the reagents are loaded into chambers A and B (and to the wells 13), and then a sealing membrane is applied to the surface 15 of the test strip 10, covering all the wells 13 and the chambers A and B. In one possible embodiment, the membrane is given a perforation or tear line adjacent to chamber A. Then, the cover member 14 is installed on the test strip 10. When the technician is ready to use the test strip 10, the user lifts up the front portion 24 of the cover to the position shown in FIG. 2. The edge 30 has a curved recess feature for the user's finger to assist in lifting up portion 24. Then, the technician grasps the free edge 32 of the membrane (shown broken away in FIG. 2 to illustrate the structure of the test strip), and pulls away the membrane such that the membrane separates at the perforation, indicated at 34. This action exposes chamber A of the dual chamber reaction vessel 12. Then, the technician introduces the fluid sample into chamber A and closes the cover member 14. The cover member 14 has additional pairs of resilient gripping legs 36 and 38 that snap onto rim features on opposite edges of the test strip, resulting in the secure engagement of the cover 14 to the test strip 10.

Figure 4A:
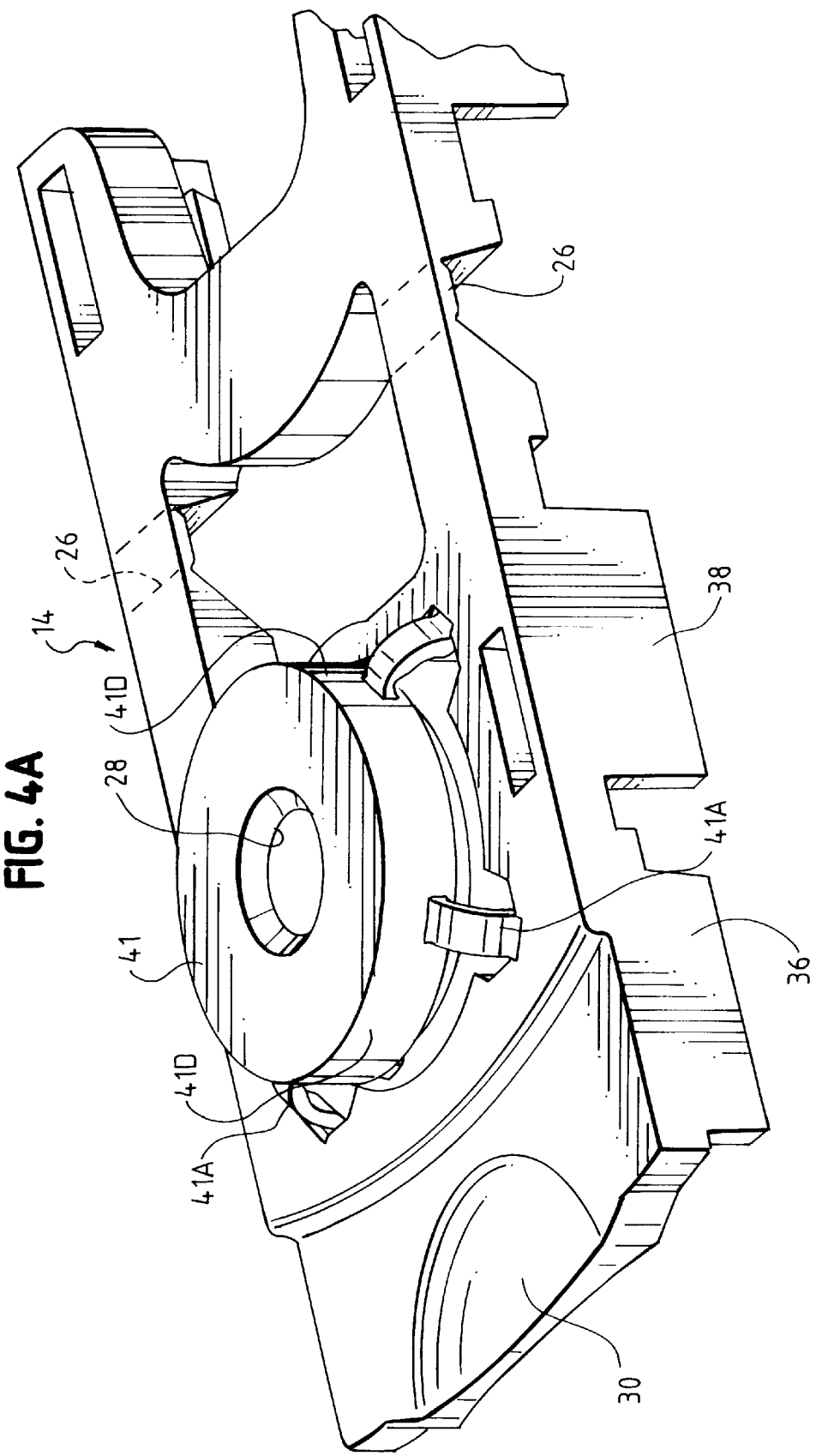
FIGS. 4A and 4B are perspective views of an alternative embodiment of the cover member.
Figure 4B:
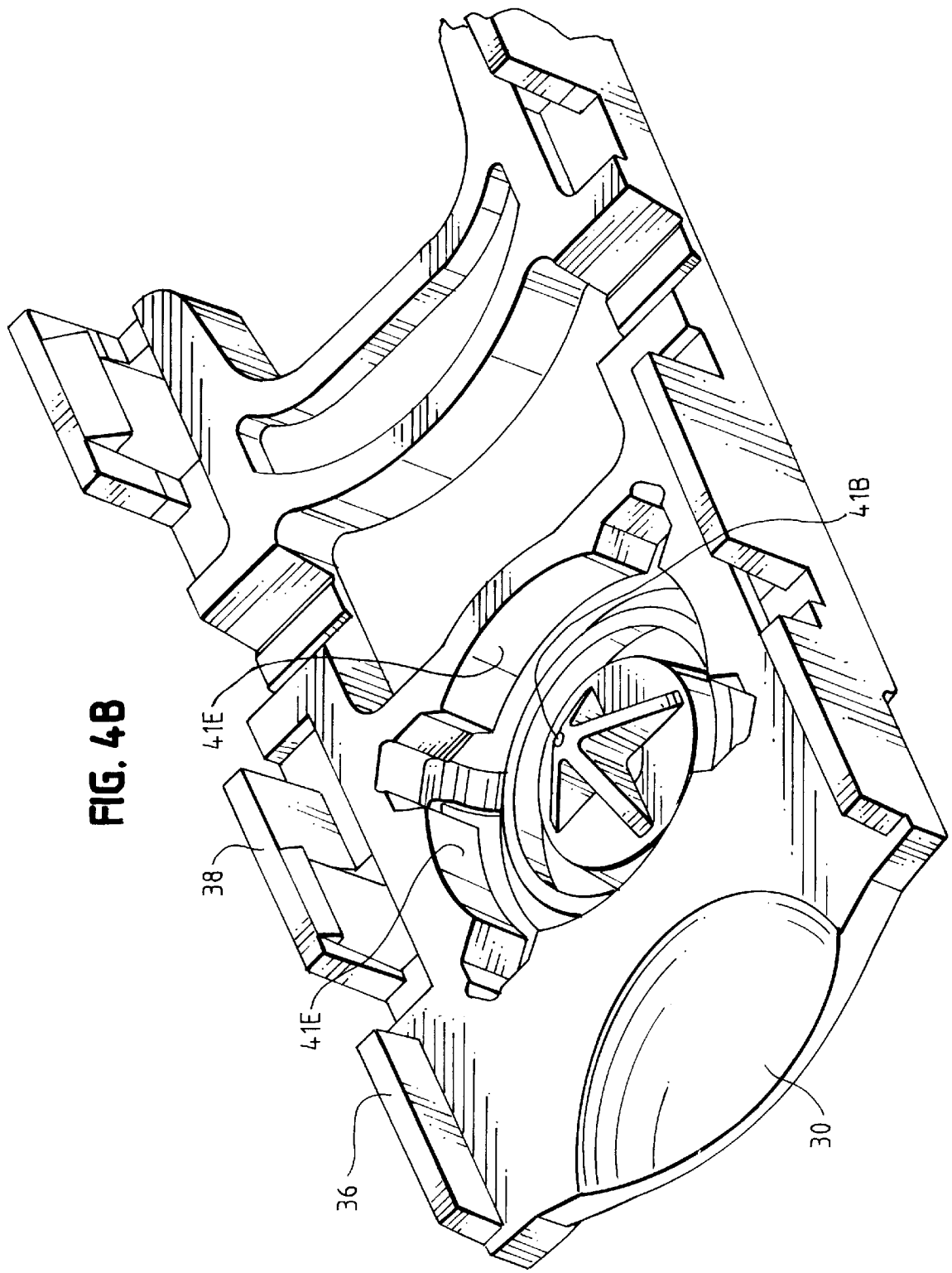

Referring to FIGS. 4A and 4B, optimally, and in the preferred embodiment, the film or membrane remains in place over chamber A and there is no tear line as just described. The cover member includes a manually actuated button 41 that has a projecting point or surface 41B on the underside thereof such that when the cover member 14 is closed by the user, the user may actuate and depress the button 41 and thereby cause the projecting point 41B to pierce the membrane covering the top of the test strip above Chamber A to provide a small opening for the introduction of the test sample. In this embodiment, the foil membrane is not removed by the technician but rather is left in place. The action of the button/projecting point is the mechanism by which chamber A is accessed at the time of use. This embodiment reduces the likelihood that any fluid or reaction solutions may unintentionally wick or migrate out of the chamber B and into the environment. As seen in FIG. 4A, the button 41 is connected to the rest of the cover by means of resilient legs 41A which allow the button 41 and projecting point 41B to move relative to the cover member and thereby pierce the membrane. Once moved the lower position, the side wall 41D of the button snugly fits within the corresponding circular wall portion 41E of the cover member 14, shown best in FIG. 4B. These figures also show the central aperture 28 that receives a porous mesh filter.

Another alternative embodiment for the cover member 14 is shown in FIGS. 4C and 4D. The button 41 is moveable from an upper position shown in FIG. 4C, in which the projecting cutting surface 41B is above the membrane (not shown) covering chamber A, to a lower position, shown in FIG. 4D, in which the projecting cutting surface 41B cuts through the membrane. The user then lifts up the end 30 of the cover member, and inserts the test sample into the small hole formed in the membrane by the cutting feature 41B. A resilient snap rim feature 41F at the lower portion of the button 41 engages a projecting shelf at the top of chamber A, as shown in FIG. 4D, thereby giving positive feel of the engagement of the button with the membrane. The user can still readily lift up the end of the cover member 14 to introduce the sample into chamber A.

Referring in particular to FIGS. 2 and 4, the cover member 14 has a void region 40 that provides access for a fork that reciprocates relative to the test strip in a processing station for the test strip. The fork, discussed subsequently in conjunction with FIGS. 19–22, operates to open a ball valve in a connecting conduit provided in the test strip that links chambers A and B of the dual chamber reaction vessel 12.

FIG. 5 is a top plan view of the test strip of FIGS. 1–3, with the cover member removed in order to better illustrate the features of the test strip per se. Referring to the right hand side of FIG. 5, a sealing membrane such as an aluminum film 42 is applied to the top surface of the test strip 10. The membrane 42, shown partially broken away, extends from the position shown in the right hand side of FIG. 5 to the left across the entire top surface of the test strip. The membrane terminates in a free end 32 adjacent to the chamber A of the dual chamber reaction vessel 12 in the vicinity of end 18A. The membrane 42 thus completely covers and seals the wells 13 of the test strip. The right hand end 18B of the test strip includes an aperture 44 for receiving an optical cuvette for the purposes of optical analysis of a detection of reaction products used in an analytical procedure for the test strip in known manner. The reaction products result from hybridization reaction(s) utilizing a solid support to capture by capture probe the reaction product, i.e., hybridization complex of amplicon and detector probe. Additional types of competitor probes may also be utilized but not detected in the hybridization reaction(s).

Referring now to the left hand side of FIG. 5, the test strip 10 includes chamber A of the dual chamber reaction vessel, a vertically-disposed connecting conduit 50 leading from the base of the test strip 10 up to the upper region thereof, and an enzyme pellet well 52 containing the amplification enzyme(s). A valve, described subsequently in conjunction with FIGS. 19–22, is located in the connecting conduit 50 and is selectively opened to allow a solution to pass from chamber A up through the connecting conduit 50 and into the enzyme pellet well 52. The passage of the solution through the enzyme pellet well dissolves the enzyme pellet. The solution enters chamber B and amplification takes place in chamber B.

The test strip 10 further includes a pair of desiccant wells 54 and 56 which are placed in air or fluid communication with chamber B. The desiccant well 54 is also shown in FIG. 6, which is a cross-sectional view of the test strip taken along the lines 6—6 of FIG. 5. The desiccant wells 54 and 56 are designed to hold a single or plurality of small desiccant pellets stacked on top of each other in the wells. During assembly of the test strip, machine inspection of the desiccant wells will confirm the quantity of desiccant pellets in the wells 54 and 56. The purpose of the desiccant is to extend the shelf life of the amplification enzyme loaded into the test strip, particularly where the amplification enzyme is in a pellet form and susceptible to degradation in the presence of a moist environment. Desiccant is particularly important to the tolerance of reagent or enzyme pellets to moisture for the extremely critical scale of enzyme and reagent concentrations provided in a gas permeable material, e.g., a test strip. In the event that the nucleotides, $MgCl_2$, primers and other reagents loaded into chamber A are in liquid form, then the desiccant wells 54 and 56 need not be placed in direct air or fluid communication with chamber A. However, in the event that the reagents in chamber A are also in pellet form or otherwise susceptible to degradation in a moist environment, then the desiccant wells will be designed and constructed to communicate with chamber A in addition to chamber B, or, alternatively, a second set of desiccant wells can be provided adjacent to chamber A to service the reagents in chamber A.

Referring in particular to FIGS. 6 and 13, the extreme lateral portion of the desiccant well 54 includes a passageway indicated by the arrows 58 in FIG. 13, indicating the air communication with the chamber B (and ultimately air communication with the enzyme pellet placed in the enzyme pellet well 52). The passageway 58 is provided above a wall 60 separating the lateral portion of the desiccant well 54 from chamber B. The two desiccant wells may accommodate different desiccant compositions having for different absorptive characteristics. Three desiccant balls 63 placed in the desiccant well 54 are indicated in phantom in FIG. 13. Alternatively, the desiccant could be in the form of a single unified desiccant body. Alternatively, the desiccant balls could be placed directly in chamber B without adverse effect on the amplification reaction, or molded into the material forming the dual chamber reaction vessel 12.

Figure 10:
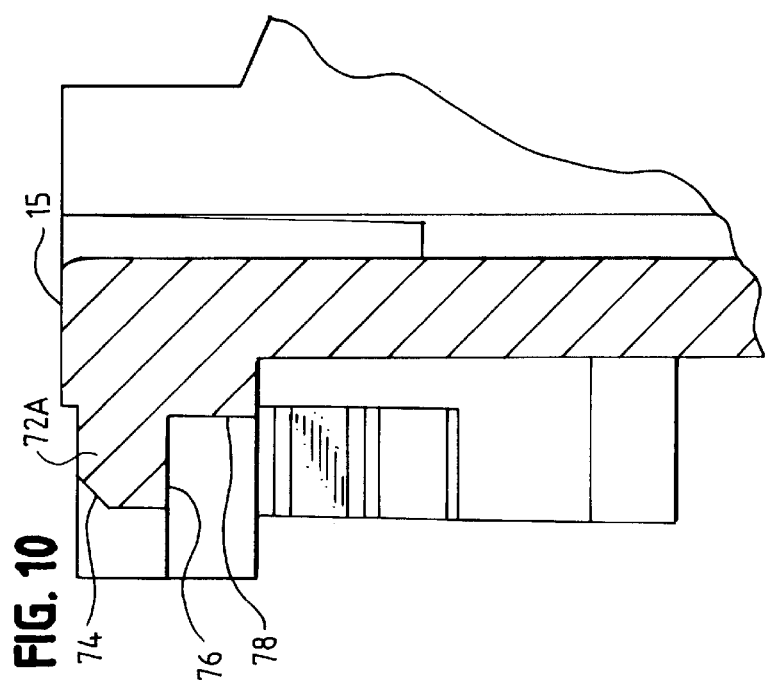
FIG. 10 is a detailed cross-sectional view of test strip, partially broken away, illustrating the locking features shown in FIG. 9.
Figure 7:
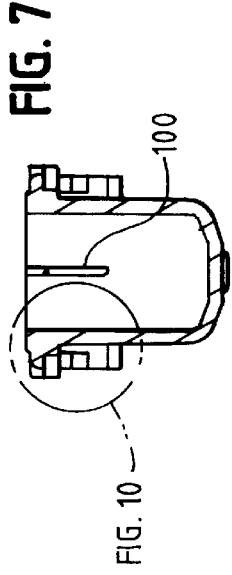
FIG. 7 is a cross-sectional view of the test strip of FIG. 5, shown along the lines 7—7 of FIG. 5.
Figure 9:
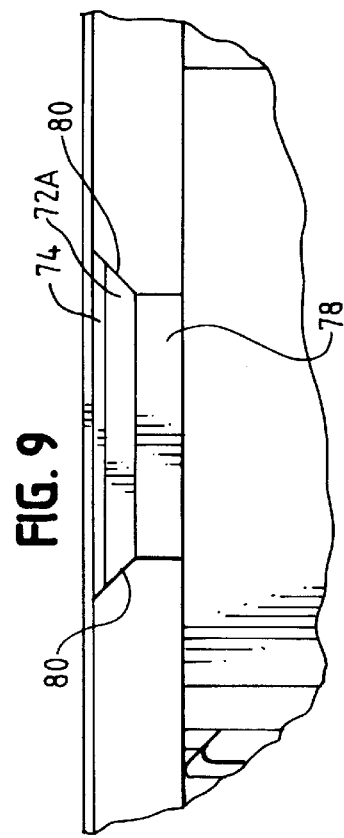
FIG. 9 is a detailed elevational view of the upper portion of the test strip in the region adjacent to the second reaction vessel, showing the features on the side of the test strip that are securely gripped by the resilient legs of the cover member to lock the cover member to the test strip.
Figure 21:
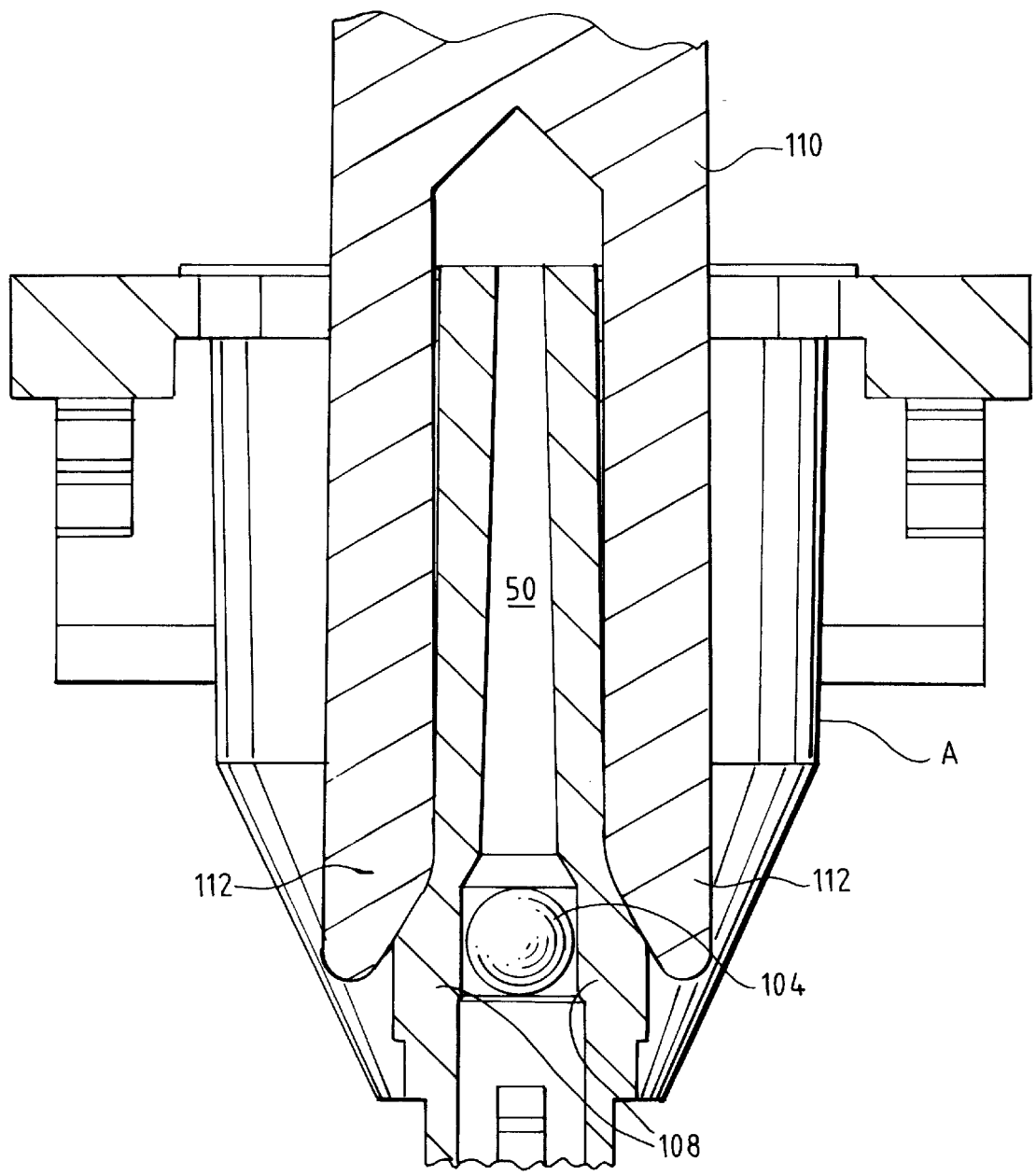
FIG. 21 is a cross-sectional view of the test strip of FIG. 5 taken in a direction transverse to the long axis of the test strip in the vicinity of the connecting conduit, showing the action of the forks of FIGS. 19 and 20 in deforming the material of the connecting conduit to thereby open the valve.

Referring to FIGS. 5 and 6, the top surface 15 of the test strip 10 includes a aperture 70 designed to accommodate the forks of FIGS. 19–21 during the process of opening the connecting conduit 50. The cover member 14 of FIGS. 3 and 4 is installed over the test strip 10 such that the aperture 40 of the cover member is directly over the aperture 70 of the test strip. FIG. 5 also shows the ledge features 72 that enable the resilient legs 20 of the cover member 14 to lock onto the test strip when the cover member is installed onto the test strip. These features are also shown in FIGS. 8–12. Referring to FIGS. 9 and 10, the test strip has a slanted portion 74 over which the wedge feature 21 (FIG. 4) of the cover member slides until the wedge feature 21 snaps under the ledge 76 and presses against the wall portion 78. The resilient nature of the legs 20 of the cover member and the action of the wedge 21 against the shelf 76 prevents the cover member 14 from becoming disengaged from the test strip during the operation of raising and lowering the front portion 24 of the cover member. The slanted surface 80 of FIG. 9 assists in installing the cover member and aligning the legs 20 relative to the ledge feature 72.

Figure 8:
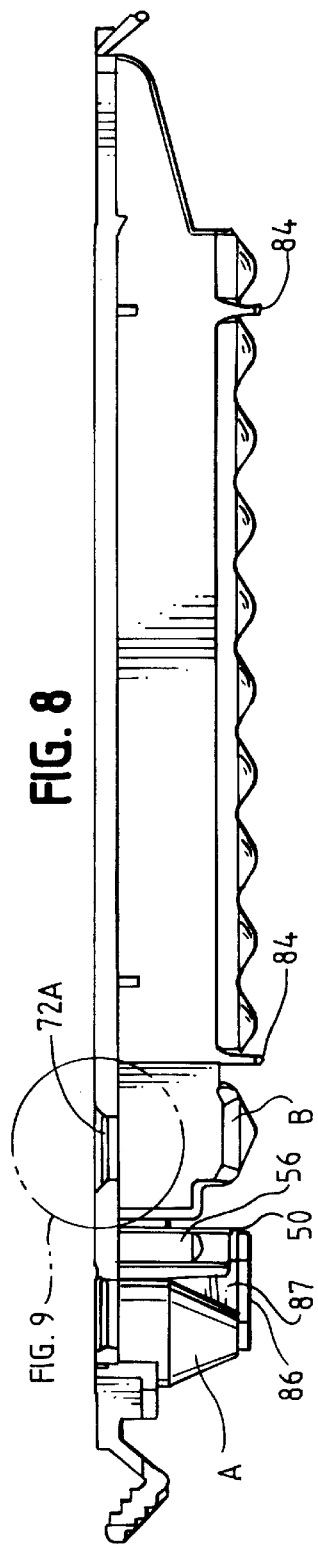
FIG. 8 is a side elevational view of the test strip of FIG. 5.

Referring to FIGS. 6 and 8, the test strip has a pair of transversely extending ridges 84 molded into the bottom of the test strip that allow the test strip to be placed in a stable, level attitude on a table top.

Figure 14:
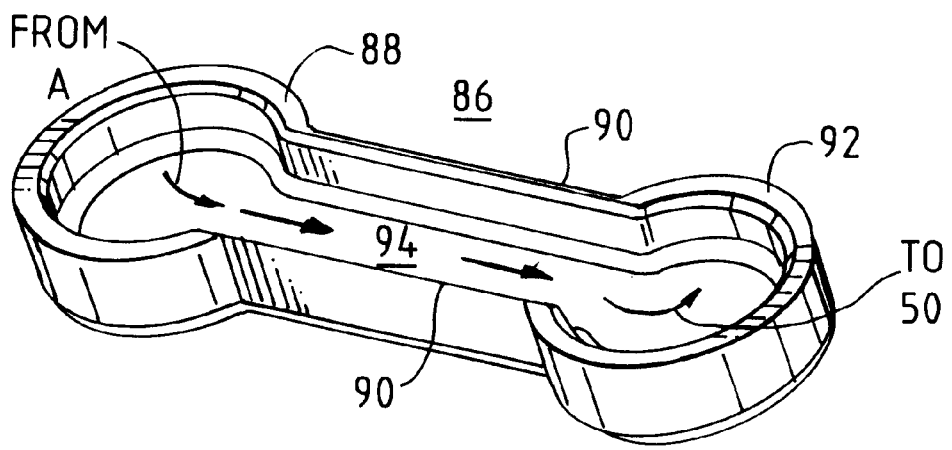
FIG. 14 is a perspective view of a cap member shown in FIG. 3 that closes off the bottom of the first reaction chamber and provides a fluid path to link the first reaction chamber to the vertically-disposed connecting conduit leading to the second reaction chamber.
Figure 15:
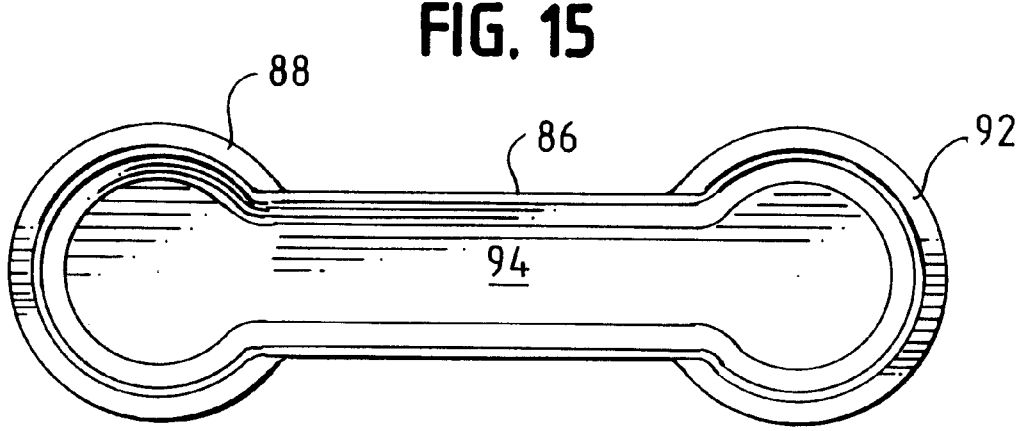
FIG. 15 is a plan view of the cap member of FIG. 14.

FIGS. 2 and 8 illustrate a base cap 86 that is manufactured separately and ultrasonically welded to the base of the test strip 10. The cap 86 covers the extreme lowermost portion of chamber A, and provides a fluid pathway for solution to pass from chamber A to the base of the vertically-disposed connecting conduit 50 and provides close contact with a TEC/heat sink thermal control system. The cap 86 is shown in greater detail in FIGS. 14 and 15. Referring to FIGS. 8 and 14–15, the cap 86 includes a semicircular portion 88 that is bonded to the base of chamber A. A pair of opposed rim elements 90 are bonded to a web portion 87 (FIG. 8) connecting chamber A to the connecting conduit 52. The cap includes another semicircular portion 92 that is bonded to a corresponding semicircular surface at the base of the connecting conduit 50. Thus, the cap forms a passageway 94 allowing fluid to pass from the base of chamber A to the base of the connecting conduit 50, as indicated by the arrows in FIG. 14.

Figure 16:
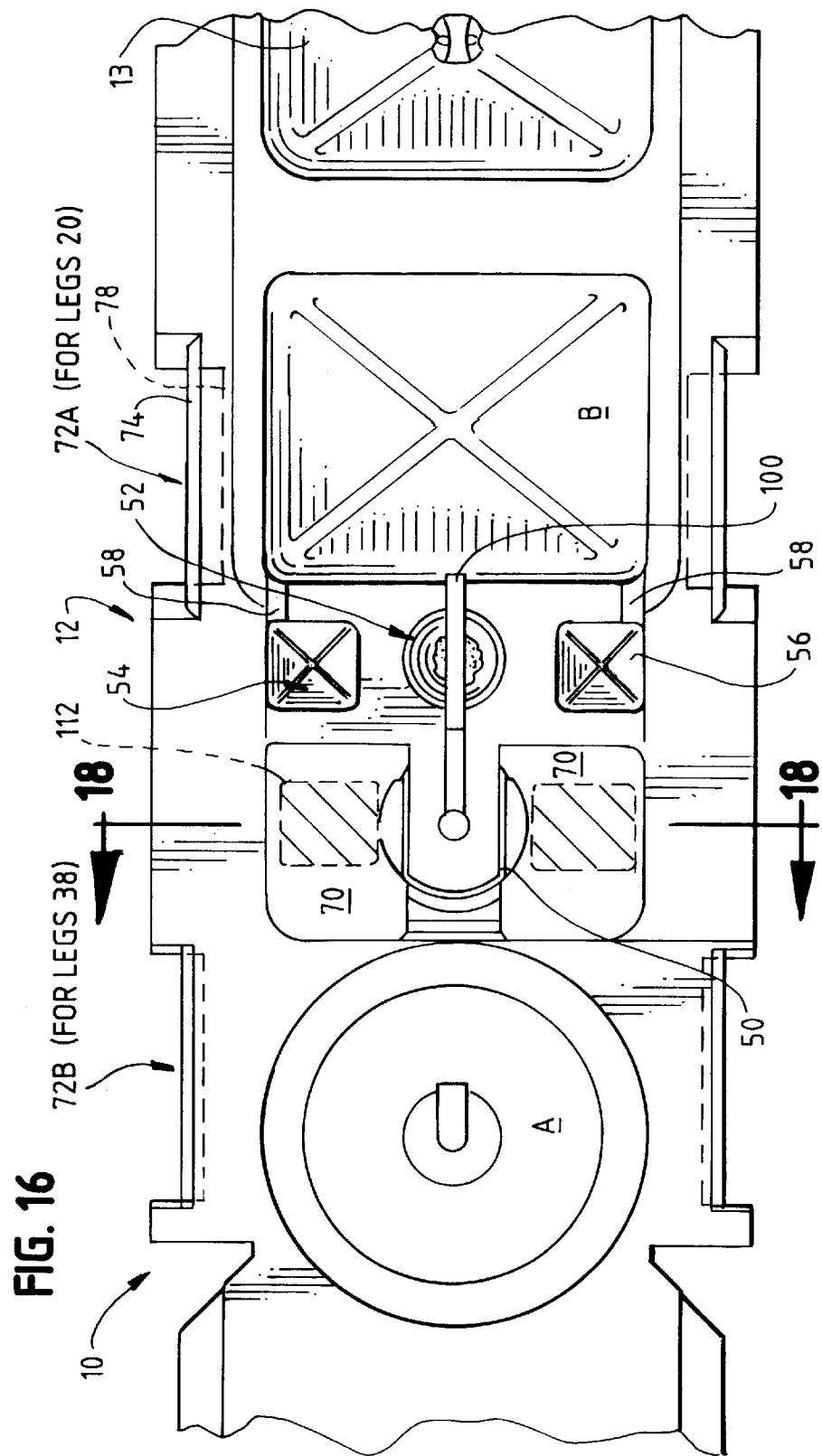
FIG. 16 is a detailed plan view of the top of the test strip of FIG. 5 in the region of the connecting conduit linking the first reaction chamber to the second reaction chamber.

FIG. 11 is a detailed cross-sectional view of the test strip of FIG. 5 taken along the lines 11 of FIG. 5, shown partially broken away, illustrating the desiccant well 56 and enzyme pellet well 52. FIG. 16 is a detailed plan view of the test strip 10, showing the structures of the dual chamber reaction vessel 12. Referring to these figures, in conjunction with FIGS. 17–22, the operation of the valve in the connecting conduit 50 and flow of solution from the reaction vessel A to the reaction vessel B will now be described in detail.

Figure 17:
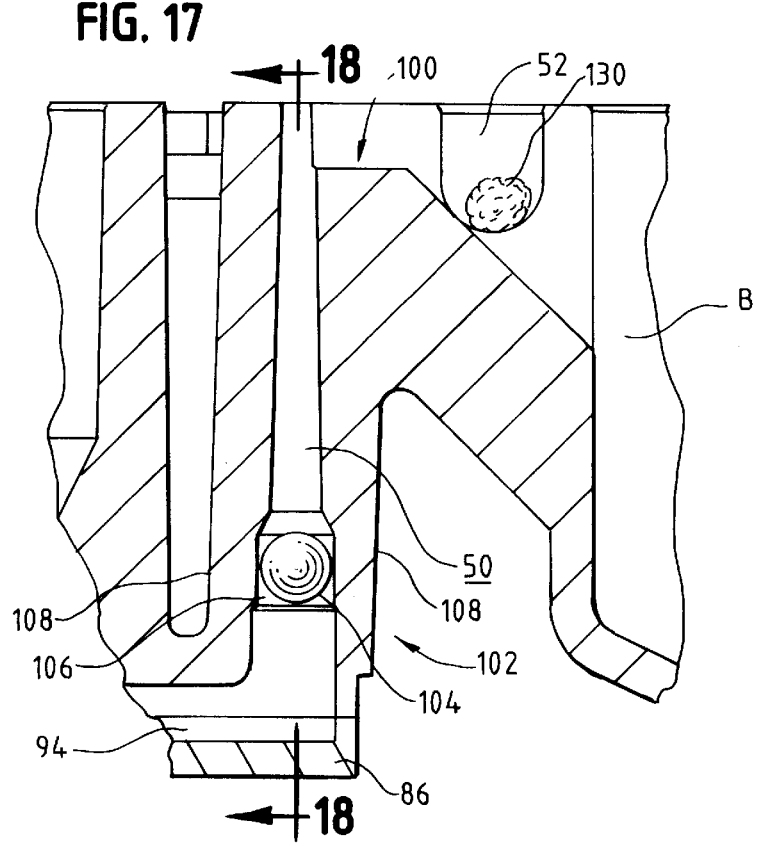
FIG. 17 is a cross-sectional view of a portion of the test strip of FIGS. 5 and 16, taken along the lines 17—17 of FIG. 16, that is, along the long axis of the test strip in the region of the connecting conduit linking the first reaction chamber to the second reaction chamber, showing the placement of a ball inside the connecting conduit that acts as a valve to close off the connecting conduit.
Figure 18:
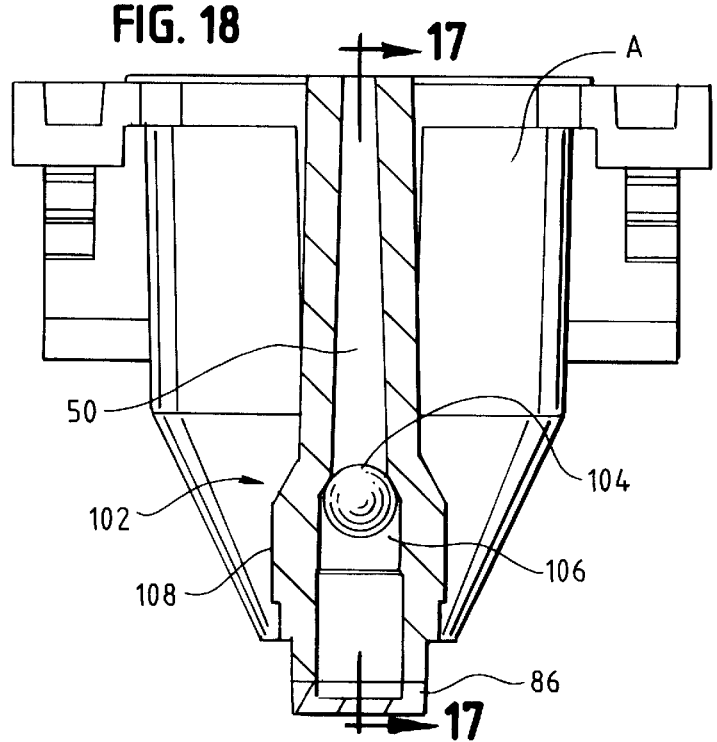
FIG. 18 is a cross-sectional view of a portion of the test strip of FIG. 5 taken in a direction orthogonal to the long axis of the capsule, along the lines 18—18 of FIGS. 16 and 17.

After the denaturation and primer annealing of the fluid sample in reaction vessel A has taken place at the first reaction temperature, a ball valve, indicated generally by reference numeral 102 in FIGS. 17 and 18, is opened. The ball valve consists of a metal ball 104 that is disposed in the connecting conduit 50 in a cylindrically-shaped intermediate region 106. The ball 104 is sized such that its diameter is slightly greater than the diameter of the intermediate region 106, thus it normally forms a complete obstruction of the connecting conduit. The walls 108 of the connecting conduit 50 are made from a deformable material (and polypropylene is sufficiently deformable for the present purposes). This deformability of the walls 108 is such that when the walls 108 are squeezed on opposite sides of the ball 104, the wall 108 is deformed in the direction perpendicular to the squeezing force, on opposite sides of the ball, to thereby create a passage for fluid around the ball.

Figure 22:
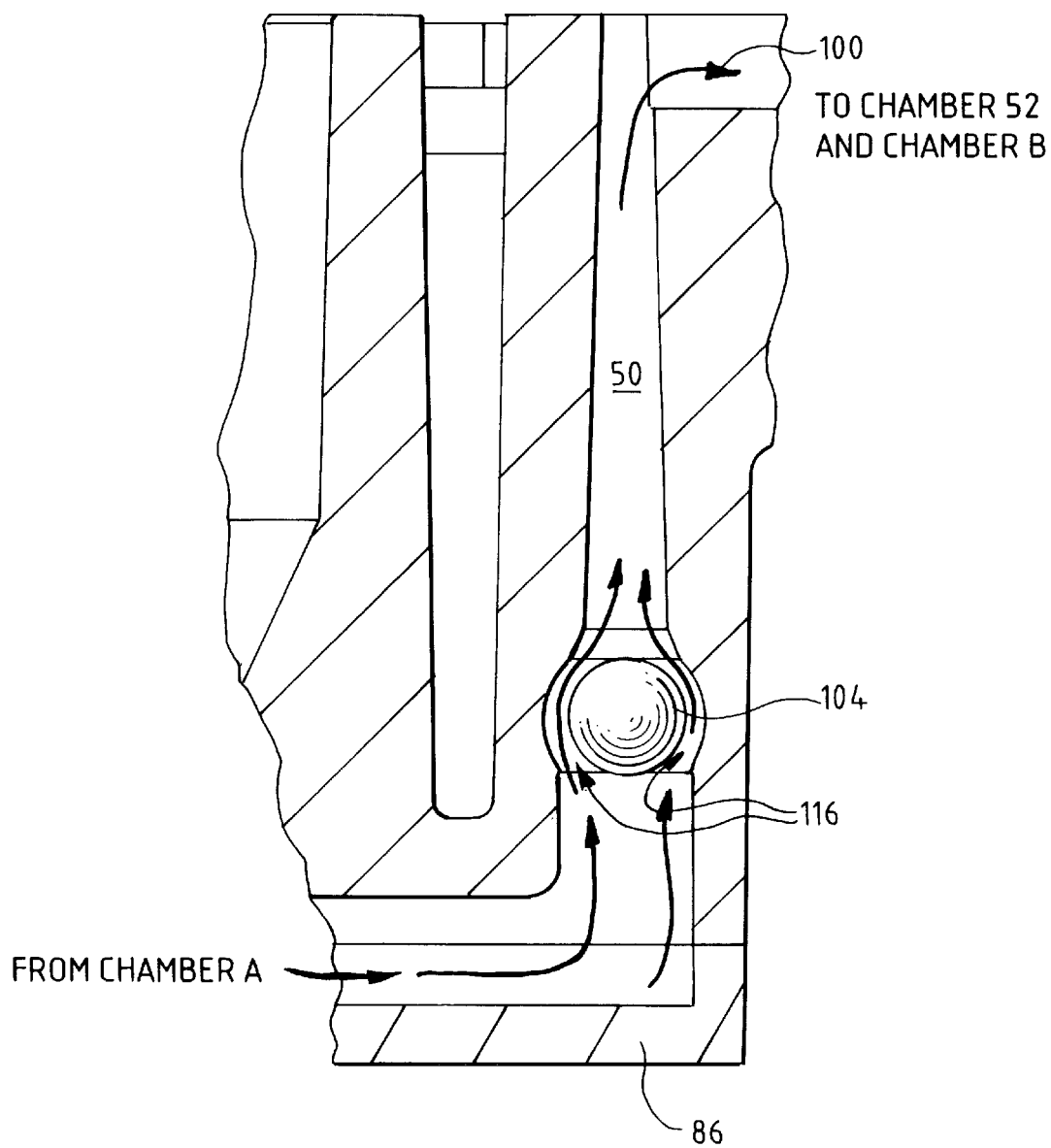
FIG. 22 is a cross-sectional view of the test strip of FIG. 22, showing the deformation of the connecting conduit and the flow of fluid through the connecting conduit.

To create this squeezing action on the walls 109 and ball 104, a fork 110 having two prongs 112 is lowered through the aperture 40 of the cover (as best shown in FIG. 19), through the aperture 70 in the top of the test strip (shown best in FIG. 16). The fork prongs 112 come into squeezing contact with the walls 108 of the connecting conduit 50 directly on opposite sides of the ball 104, as shown best in FIG. 21. This squeezing action deforms the walls 108, as shown in FIG. 22, to form passages 116 on opposite sides of the ball 104.

Simultaneous with the opening of the ball valve as just described, a vacuum is drawn on the test strip, and particularly on the first reaction chamber A. This is achieved by placing the test strip in a reaction processing station that includes a vacuum enclosure around the test strip and evacuating the air in the vacuum enclosure. The drawing of the vacuum lowers the pressure in both the first and second chambers A and B, since they are now in air and fluid communication with one another. When the vacuum is released, a pressure gradient exists between chamber A and chamber B, with chamber A at a higher pressure. The pressure gradient forces the fluid solution in chamber A through the passage 94 in the cap 86 (see FIGS. 14 and 15), up and around the passages 116 in the connecting conduit 50 as indicated by the arrows in FIG. 22, and up to the top of the connecting conduit 50.

Once the fluid solution has reached the top of the connecting conduit 50, the fluid enters a channel 100 (see FIGS. 16 and 17) leading to the enzyme pellet well 52. The fluid dissolves the enzyme pellet 130 (FIG. 17) in the well 52, and carries the amplification enzyme into chamber B. The amplification of the nucleic acid in the fluid sample occurs in chamber B at the specified temperature, e.g., 42 degrees C.

Referring now to FIGS. 19 and 20, the, reciprocating action of the fork 110 opening the ball valve in shown schematically. In FIG. 19, the test strip 10 is shown with the sealing membrane 42 applied to the top surface of the test strip in the manner described previously, as it would be when the device is manufactured and ready for use. The membrane 42 carries a bar code identifying the type of test strip that is being used or other pertinent information.

In FIG. 20, the forks 20 are shown in conjunction with an amplification processing station of the type described in U.S. Pat. No. 5,786,182. The station is shown in an end view, partially in section, with two test strips 10 installed in the station. The forks are shown integral to a cross-member 132 that is in turn bolted to the top of a vacuum cover housing 134 in the amplification processing station. The test strips 10 are installed on a TEC/heat sink assembly 136 that maintains the two chambers of the dual chamber reaction vessel in the test strips 10 at the proper temperature, as described in detail in U.S. Pat. No. 5,786,182. The vacuum cover housing 134 is attached to a mechanical drive mechanism that raises and lowers the vacuum cover housing relative to a horizontal support member 138. The cover housing 134 and support member 138 define a vacuum enclosure or chamber 140. The vacuum cover housing 134 further includes ports (not shown) for withdrawing air from the vacuum enclosure 140 and introducing air back into the vacuum enclosure 140. When the vacuum cover housing 134 is lowered down onto the support member 138, it forms an air-tight seal with the support member 138 (using a suitable gasket structure in the region 139), enabling vacuum to be drawn in the enclosure. The drawing of vacuum in the enclosure 140 causes air to be withdrawn from the dual chamber reaction vessel via the aperture 28 in the cover member 14 and an air-permeable filter 142 placed therein (see FIG. 19). Then, when the vacuum is released in the enclosure 140, with the housing 134 remaining in the lower position during the release of vacuum, the pressure differential between chambers A and B causes fluid solution in chamber A to migrate through the connecting conduit, opened by the action of the forks 110, and into the enzyme pellet chamber and chamber B, in the manner described previously.

Further details on a presently preferred amplification station incorporating the vacuum and other features of FIG. 20 are described in the application of Bryan Kluttz et al. filed concurrently, cited previously.

While the above ball-valve embodiment is a presently preferred embodiment, it will be appreciated that numerous other equivalent and alternate mechanisms may be incorporated into a test device for purposes of allowing fluid to migrate or transfer from chamber A to chamber B. Several different mechanisms are described in the U.S. Pat. No. 5,786,182. Still other different valve mechanisms may exist or may be developed by persons skilled in the art. The particular details of the valve mechanism are not considered particularly important to the present invention. Obviously, if a different valve mechanism is used, then the amplification reaction processing station that processes the test strip may have a different type of valve opening mechanism besides the forks of FIG. 20. Accordingly, the details of the station processing the test device may have different operational features to work with the particular valve or connecting conduit mechanisms that are incorporated into the dual chamber reaction vessel.

Figure 23:
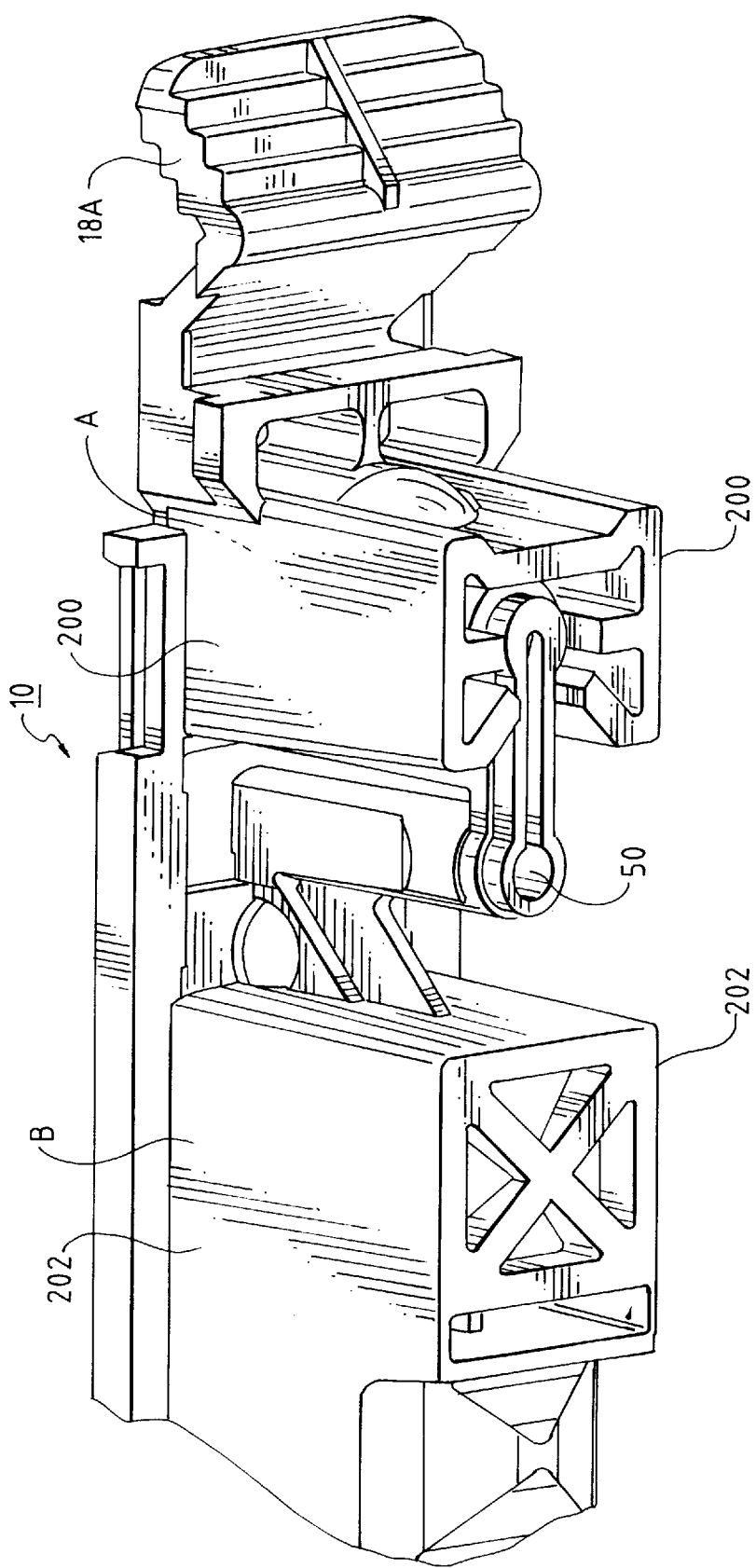
FIG. 23 is a perspective view of an alternative embodiment of a test strip in which the walls of the test strip forming the first and second reactions chambers have exterior surfaces configured to engage heated surfaces in a nucleic acid amplification station processing the test strips to assist in maintaining the two chambers at desired temperatures.

FIG. 23 is a perspective view of an alternative embodiment of the test strip in which the chamber A of the dual chamber reaction vessel has an exterior surface arrangement designed to come into close proximity or contact with a TEC/heat sink assembly in an amplification reaction processing station in order to promote rapid heat transfer between chamber A and the TEC/heat sink assembly. In particular, the wall structure forming chamber A has opposed sides 200 which provide an extended surface area to contact and transfer heat from a heated surface in the amplification station into the interior of chamber A, Similarly, the wall structure 202 forming chamber B has extended planar surfaces 202 on opposite sides thereof to transfer heat into the interior of chamber B. Note that FIG. 23 shows the test strip from below, prior to the securing of the base cap 86 (see FIGS. 8, 14 and 15) to the features connecting chamber A with the vertically disposed connecting conduit 50.

From the above discussion, it will be readily apparent that the present invention is not intended to be limited to illustrated embodiment. Persons of skill in the art will appreciate that many variations may be made to the preferred and alternative embodiments described above without departure from the true spirit and scope of the invention. This true spirit and scope is to be determined by reference to the appended claims, interpreted in light of the foregoing specification.

What is claimed is:

1. A test device for performing a nucleic acid amplification reaction, comprising:
   a housing having a first end and a second end, said housing having a portion thereof defining a plurality of wells between said first and second ends;
   said housing further comprising a dual chamber reaction vessel for a nucleic acid amplification reaction to be carried out therein, said dual chamber reaction vessel comprising a first chamber in which a first portion of a nucleic acid amplification reaction is performed, a second chamber in which a second portion of a nucleic acid amplification reaction is performed, an openable connecting conduit linking said first chamber to said second chamber and an externally actuated valve disposed in said openable connecting conduit, wherein an actuation of said valve opens said connecting conduit and allows fluid to flow through said connecting conduit from said first chamber to said second chamber.

2. The test device of claim 1, wherein said test device has a reagent inserted into said first chamber and a second reagent inserted into or placed in fluid communication with said second chamber, and wherein said test device further comprises a membrane affixed to said housing, said membrane applied to said housing to cover said first and second chambers and said wells after insertion of said first and second reagents into said test device.

3. The test device of claim 2, further comprising a cover member secured to said housing and overlying said membrane and said first and second chambers, wherein said cover member is moveable relative to said first chamber to thereby allow a user to access an opening in said membrane and introduce a sample into said first chamber.

4. The test device of claim 3, wherein said membrane comprises a first portion covering said first chamber and a second portion covering said second chamber and a third portion separating said first and second portions, wherein said cover member is moveable relative to said first chamber to allow a user to tear or perforate said third portion and thereby remove said first portion of said membrane from said test device.

5. The test device of claim 3, wherein said cover member further comprises:
   a first portion, a hinge, and a second portion, said first portion covering said first chamber in a first position, said first portion moveable relative to said first chamber via said hinge to an elevated position enabling a user to access said first chamber, said second portion engaging said test device.

6. The test device of claim 5, wherein said first portion of said cover member further comprises an aperture in said first portion placed in registry with said first chamber when said first portion is in said first position, and wherein an absorbent mesh filter is placed within said aperture.

7. The test device of claim 1, wherein said test device further comprises at least one desiccant chamber for containing a desiccant, said desiccant chamber located on said test device in air or fluid communication with at least one of said first and second chambers, or both, of said dual chamber reaction vessel.

8. The test strip of claim 7, wherein said test device comprises two or more desiccant chambers for containing a desiccant, said two or more desiccant chambers located on said test device in air or fluid communication with at least one of said first and second chambers, or both, of said dual chamber reaction vessel.

9. The test device of claim 7, wherein said desiccant is in a pellet form.

10. The test device of claim 1, wherein a desiccant is loaded directly into at least one of said first and second chambers, or both, of said dual chamber reaction vessel.

11. The test device of claim 1, wherein said test device is made from a molded material and wherein a dessicant is molded into said test strip in the region of at least one of said first and second chambers.

12. The test device of claim 1, wherein said housing is in a form of an elongate strip with said wells spaced in an array along said strip, and wherein said second chamber is arranged in an aligned condition relation relative to said wells.

13. The test device of claim 1, wherein said test device further comprises an optical cuvette.

14. The test device of claim 1, wherein said dual chamber reaction vessel is integrally formed with said housing.

15. The test device of claim 1, wherein said housing comprises an aperture adjacent to said first end, and wherein said dual chamber reaction vessel comprises a separable piece inserted into said aperture.

16. The test device of claim 1, wherein said first and second chambers of said dual chamber reaction vessel further comprise a wall portion forming said first and second chambers having an exterior surface, and wherein said exterior surface of said wall portion is configured to come into touching contact with a heat sink having a predetermined form in a processing station for said test device.

17. A dual chamber disposable reaction vessel for a nucleic acid amplification reaction, comprising:
   a first chamber for performing a first portion of a first nucleic acid amplification reaction,
   a second chamber for performing a second portion of a nucleic acid amplification reaction,
   a connecting conduit linking said first chamber to said second chamber,
   a valve disposed in said connecting conduit controlling the flow of a fluid sample from said first chamber to said second chamber;
   an enzyme pellet chamber disposed between said connecting conduit and said second chamber and adapted to contain an amplification enzyme pellet, such that said fluid sample passing from said first chamber to said second chamber passes through said enzyme pellet chamber; and a membrane covering said first and second chambers.

18. The dual chamber disposable reaction vessel of claim 17, further comprising:

at least one desiccant chamber in communication with at least one of said first and second chambers, or both of said first and second chambers.

19. The dual chamber disposable reaction vessel of claim 17, wherein said dual chamber reaction vessel is contained in a disposable testing device comprising said dual chamber reaction vessel, at least one wash well, and a detection well.

20. The dual chamber reaction vessel of claim 17, wherein said dual chamber reaction vessel is contained in a disposable testing device comprising said dual chamber reaction vessel, and a decontamination well.

21. The dual chamber disposable reaction vessel of claim 19, wherein said testing device comprises an elongate strip.

22. The dual chamber disposable reaction vessel of claim 20, wherein said testing device comprises an elongate strip.

23. A method of constructing a unit dose nucleic acid amplification reaction testing apparatus, comprising the steps of:

forming a test device having (1) a dual chamber disposable reaction vessel comprising a first chamber, a second chamber, and a connecting conduit linking said first chamber with said second chamber, and (2) at least one intermediate processing well;

adding a first reagent to said first chamber;

adding a second reagent into said test device either in said second chamber or in an intermediate chamber in fluid communication with said second chamber; and affixing a sealing membrane to said test device in a manner to cover said first and second chambers.

24. The method of claim 23, further comprising the step of affixing a cover member to said test device, said cover member moveable relative to first chamber to thereby allow access to said sealing film.

25. The method of claim 23, further comprising the step of affixing a base cap to said test device, said cap forming a channel between said first chamber and said connecting conduit.

26. The method of claim 23, further comprising the step of adding a desiccant into said test device in air communication with either said first reagent or said second reagent, or both said first and second reagent.

27. A method of performing a nucleic acid amplification reaction, comprising the steps of:

(1) providing a dual chamber reaction vessel ready for use in performing a nucleic acid amplification reaction, said vessel comprising a first reaction chamber, a second reaction chamber, a connecting conduit linking said first reaction chamber to said second reaction chamber and an externally actuated valve disposed in said connecting conduit, wherein an actuation of said valve opens said connecting conduit and allows fluid to flow through said connecting conduit from said first chamber to said second chamber; comprising the steps of placing a first reagent in fluid communication with said first reaction chamber and a second reagent in fluid communication with said second reaction chamber; and sealing said first and second reaction chambers and said reagents from the environment; and (2) conducting a nucleic acid amplification reaction in said vessel while maintaining a temperature differential between said first reaction chamber and the environment surrounding said second reagent, comprising the steps of:

introducing a sample into said first reaction chamber;

placing said first reaction chamber at a first temperature and conducting a first portion of said nucleic acid amplification reaction in said first reaction vessel at said first temperature;

actuating said valve and transferring a portion of the contents of said first reaction vessel to said second reaction chamber; and placing said second reaction chamber at a second temperature different from said first temperature and conducting a second portion of said nucleic acid amplification reaction in said section reaction chamber at said second temperature.

28. The method of claim 27, wherein said dual chamber reaction vessel is embodied in a test strip having a plurality of wells arranged in array.

29. The method of claim 28, wherein said test strip has a major and minor axis having a predetermined length and width, respectively, said length and width selected such that said test strip is compatible with a detection instrument.

30. The method of claim 27, further comprising loading a desiccant into said dual chamber reaction vessel in air or fluid communication with at least one of said first and second reaction chambers, or both said first and second reaction chambers.

31. The method of claim 27, further comprising the step of affixing a cover to said dual chamber reaction vessel, wherein said cover is moveable relative to said first chamber to allow a user access to said first reaction chamber.

32. The method of claim 27, wherein said step of transferring comprises the step of drawing a vacuum on said dual chamber reaction vessel and drawing said at least a portion of the contents of said first chamber into said second chamber.

33. The method of claim 27, wherein said step of transferring comprises the step placing said dual chamber reaction vessel in a vacuum enclosure, applying vacuum to said vacuum enclosure, and then releasing said vacuum.

34. The test device of claim 1, further comprising a cover member adapted for covering at least a portion of said housing, said cover member moveable relative to said housing so as to provide access to said dual chamber reaction vessel.

35. The test device of claim 34, wherein said cover member further comprises a button moveable relative to said housing having said cutting surface, said button operable to pierce a membrane applied to said housing in a manner to cover said dual chamber reaction vessel.

36. The test device of claim 34, wherein said cover member further comprises an aperture for receiving therein a porous filter, said cover mountable to said housing such that said porous filter is in registry with said first chamber of said dual chamber reaction vessel.

37. The test device of claim 34, wherein said cover member further comprises resilient snap means for releasably engaging said cover member to said housing.

* * * * *